(12) United States Patent
Ahmed

(10) Patent No.: US 9,707,391 B2
(45) Date of Patent: *Jul. 18, 2017

(54) METHOD FOR MODULATION OF EFFECTOR ORGANS

(71) Applicant: The Research Foundation of the City University of New York, New York, NY (US)

(72) Inventor: Zaghloul Ahmed, Staten Island, NY (US)

(73) Assignee: The Research Foundation of the City University of New York, New York, NY (US)

(\*) Notice: Subject to any disclaimer, the term of this patent is extended or adjusted under 35 U.S.C. 154(b) by 0 days.

This patent is subject to a terminal disclaimer.

(21) Appl. No.: 15/190,088

(22) Filed: Jun. 22, 2016

(65) Prior Publication Data

US 2016/0339238 A1 Nov. 24, 2016

Related U.S. Application Data

(63) Continuation-in-part of application No. 15/046,797, filed on Feb. 18, 2016, which is a continuation of application No. 14/579,829, filed on Dec. 22, 2014, now Pat. No. 9,283,391.

(60) Provisional application No. 62/092,214, filed on Dec. 15, 2014, provisional application No. 61/925,423, filed on Jan. 9, 2014, provisional application No. 61/919,806, filed on Dec. 22, 2013, provisional application No. 62/183,045, filed on Jun. 22, 2015.

(51) Int. Cl.
| | | |
|---|---|---|
| *A61N 1/20* | (2006.01) |
| *A61N 1/05* | (2006.01) |
| *A61N 1/36* | (2006.01) |
| *A61F 7/08* | (2006.01) |
| *A61F 7/10* | (2006.01) |

(52) U.S. Cl.
CPC ............ *A61N 1/205* (2013.01); *A61F 7/08* (2013.01); *A61F 7/10* (2013.01); *A61N 1/0551* (2013.01); *A61N 1/20* (2013.01); *A61N 1/36003* (2013.01); *A61N 1/36157* (2013.01)

(58) Field of Classification Search
CPC .. A61N 1/36157; A61N 1/36003; A61N 1/20; A61N 1/0551; A61N 1/205
See application file for complete search history.

(56) References Cited

U.S. PATENT DOCUMENTS

| | | | |
|---|---|---|---|
| 6,366,814 B1 | 4/2002 | Boveja et al. | |
| 9,283,391 B2 \* | 3/2016 | Ahmed | .............. A61N 1/36157 |
| 2003/0225331 A1 \* | 12/2003 | Diederich | ................ A61N 7/02 |
| | | | 600/437 |

(Continued)

OTHER PUBLICATIONS

International Search Report and Written Opinion of the International Searching Authority dated Dec. 1, 2016 from parent International Application No. PCT/US16/38815 filed on Jun. 22, 2016.

*Primary Examiner* — Catherine Voorhees
(74) *Attorney, Agent, or Firm* — Burns & Levinson LLP; Orlando Lopez; Janine M. Susan

(57) ABSTRACT

Modulation of target effector organs in vertebrate beings using direct current stimulation for stimulation of spinal cord at regions of autonomic innervation, using direct current for peripheral nerve stimulation, by modulating central autonomic outflow and combinations thereof.

26 Claims, 23 Drawing Sheets

(56) References Cited

U.S. PATENT DOCUMENTS

| | | |
|---|---|---|
| 2004/0111126 A1 | 6/2004 | Tanagho et al. |
| 2004/0210261 A1 | 10/2004 | King et al. |
| 2007/0073357 A1 | 3/2007 | Rooney et al. |
| 2007/0156179 A1* | 7/2007 | S.E. .................. A61N 1/36089 607/2 |
| 2009/0157138 A1* | 6/2009 | Errico ................ A61N 1/36007 607/40 |
| 2013/0035745 A1 | 2/2013 | Ahmed et al. |
| 2013/0072998 A1 | 3/2013 | Su et al. |
| 2013/0261696 A1 | 10/2013 | Thacker et al. |
| 2014/0039336 A1 | 2/2014 | Osorio et al. |
| 2014/0180361 A1 | 6/2014 | Burdick et al. |
| 2016/0158542 A1* | 6/2016 | Ahmed .............. A61N 1/36157 607/48 |
| 2016/0339237 A1* | 11/2016 | Ahmed ................. A61N 1/205 |

* cited by examiner

SEGMENTAL PARA-SYMPATHETIC INNERVATION

| LOCATION OR ORGAN | SPINAL LEVEL |
|---|---|
| HEAD AND NECK | CN 3, 7, 9 |
| HEART | CN 10 |
| BRONCHI AND LUNGS | CN 10 |
| ESOPHAGUS | CN 10 |
| STOMACH | CN 10 |
| SMALL INTESTINE | CN 10 |
| LARGE INTESTINE (TO SPLENIC FLEXURE) | CN 10 |
| LARGE INTESTINE (SPLENIC FLEXURE TO RECTUM) | S2-4 |
| LIVER AND GALLBLADDER | CN 10 |
| SPLEEN | CN 10 |
| PANCREAS | CN 10 |
| KIDNEY | CN 10 |
| SUPRARENAL | NONE |
| URINARY BLADDER | S2-4 |

SEGMENTAL SYMPATHETIC INNERVATION

| LOCATION OR ORGAN | SPINAL LEVEL |
|---|---|
| HEAD AND NECK | T1-5 |
| HEART | T1-5 |
| BRONCHI AND LUNGS | T2-4 |
| ESOPHAGUS | T5-6 |
| STOMACH | T6-10 |
| SMALL INTESTINE | T9-10 |
| LARGE INTESTINE (TO SPLENIC FLEXURE) | T11-L1 |
| LARGE INTESTINE (SPLENIC FLEXURE TO RECTUM) | L1-2 |
| LIVER AND GALLBLADDER | T7-9 |
| SPLEEN | T6-10 |
| PANCREAS | T6-10 |
| KIDNEY | T10-L1 |
| SUPRARENAL | T8-L1 |
| URINARY BLADDER | T11-L2 |

FIG. 2

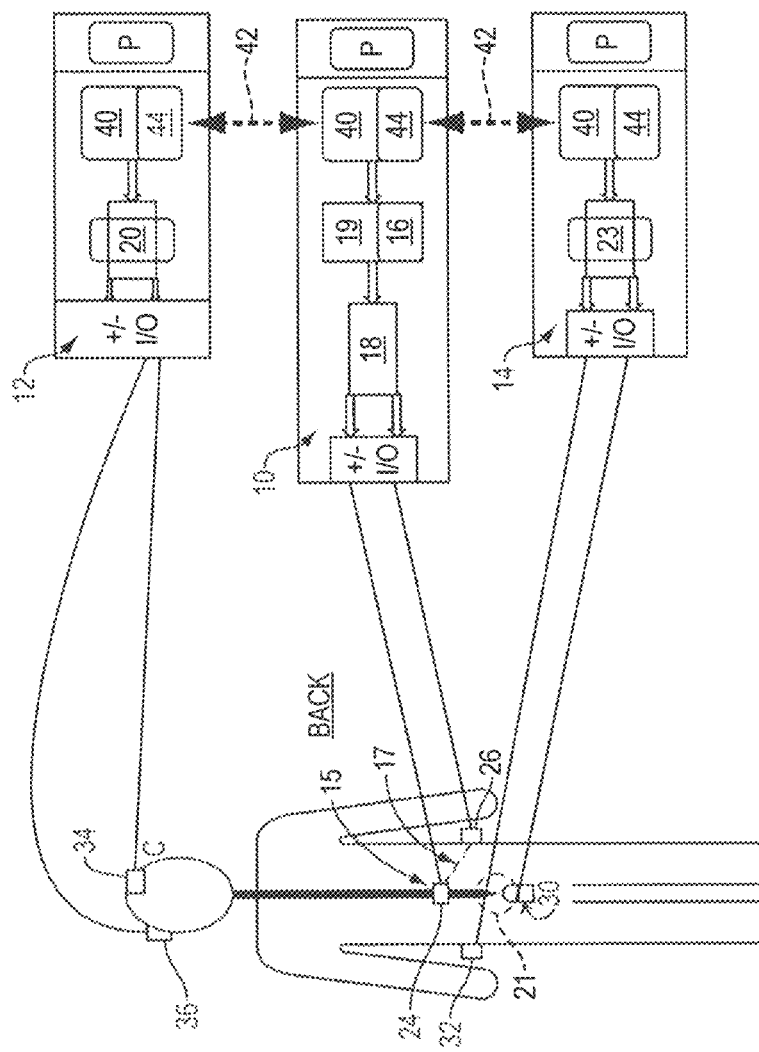
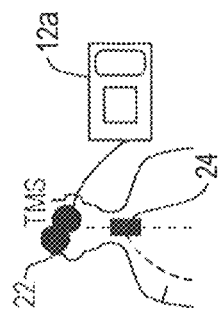
FIG. 4A
FIG. 4B

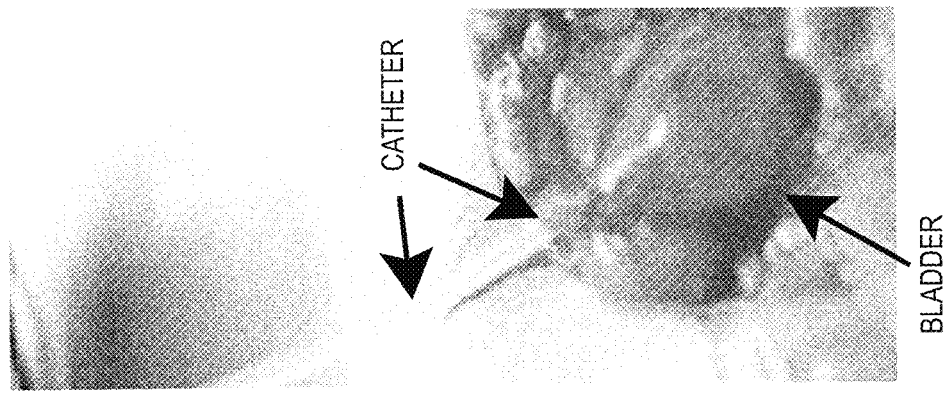
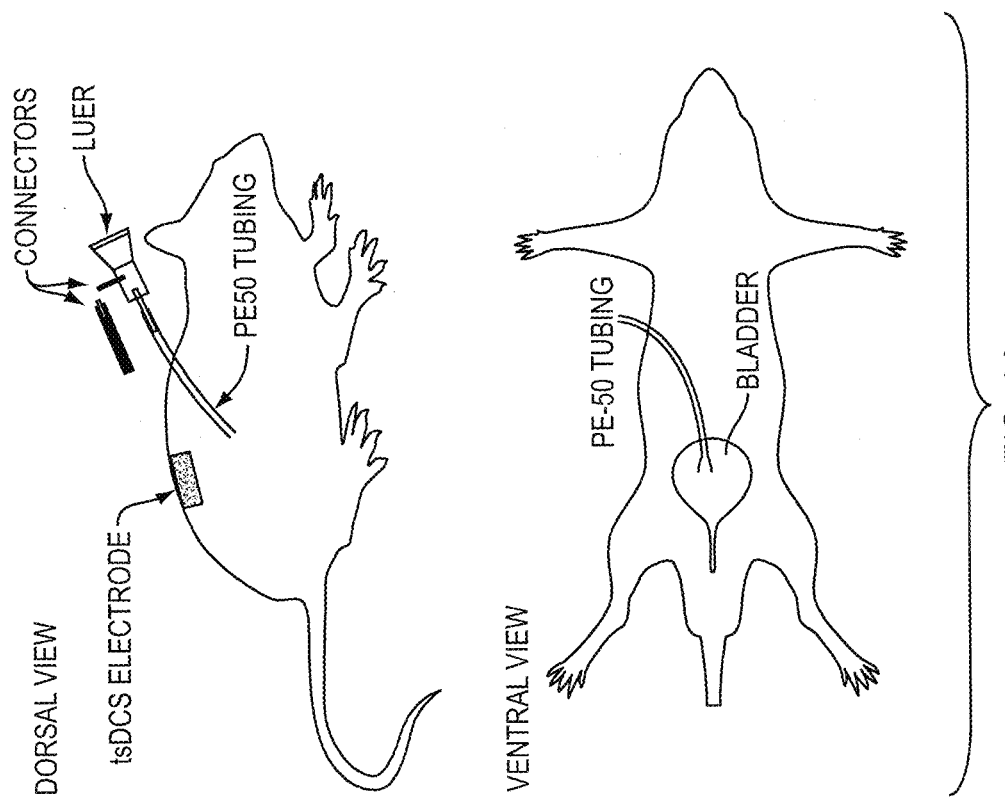
FIG. 6B
FIG. 6A

SYMPATHOMIMETICS
- AMPHETAMINES
- PHENYLEPHRINE

PARASYMPATHOLYTICS
- SCOPOLAMINE
- ATROPINE

TRANSDERMAL DELIVERY

PARASYMPATHOMIMETICS
- MUSCARINE
- PILOCARPINE
- CHOLINE ESTERS

SYMPATHOLYTICS
- PRAZOSIN
- YOHIMBINE

METHOD FOR MODULATION OF EFFECTOR ORGANS

CROSS-REFERENCE TO RELATED APPLICATIONS

This application claims is a continuation-in part of co-pending U.S. application Ser. No. 15/046,797, filed Feb. 18, 2016, which is a continuation of U.S. application Ser. No. 14/579,829, filed Dec. 22, 2014, entitled: Trans-spinal Direct Current Stimulation Systems, which claims Priority of U.S. Provisional Application Ser. 62/092,214, filed Dec. 15, 2014, entitled: Trans-spinal Direct Current Stimulation Systems, U.S. Provisional Application Ser. 61/925,423, filed Jan. 9, 2014, entitled: Method and Apparatus for Safe Regulation of Muscle Tone, and U.S. Provisional Application Ser. 61/919,806, filed Dec. 22, 2013, entitled: Method and Apparatus for Regulation of Muscle Tone. Priority is also claimed upon U.S. Provisional Application Ser. No. 62/183,045, filed Jun. 22, 2015, entitled MODULATION OF BLADDER FUNCTION USING tsDCS.

All of the foregoing are incorporated herein by reference in their entirety for all purposes whatsoever.

FIELD

The present invention relates to method and apparatus for modulating and regulating autonomically-innervated effector organs, such as modulation and regulation of bladder function.

BACKGROUND

The nervous system includes the Central Nervous System (CNS) and the Peripheral Nervous System (PNS), the latter including the Somatic Nervous System (SNS) and Autonomic Nervous System (ANS). The CNS includes the brain and the spinal cord. The spinal cord is the main communication route for signals between the body and the brain. The SNS and ANS overlap the CNS and PNS. There are 31 pairs of spinal nerves arising from cervical (8), thoracic (12), lumbar (5), sacral (5) and coccygeal (1) segments. The spinal nerves contain both sensory and motor fibers. Efferent nerves (as opposed to afferent nerves) are the nerves leading from the central nervous system to an effector organ, and efferent neural signals refer to neural signals from the brain that are transmitted via spinal cord pathways to effector organs. Afferent nerves are the nerves leading to the central nervous system, and afferent neural signals refer to neural signals being transmitted to the brain.

The ANS consists of two divisions, the sympathetic nervous system and the parasympathetic nervous system, FIG. 1, and is responsible for regulating bodily functions including heart rate, respiration, digestion, bladder tone, sexual response and other functions. Activation of the sympathetic nervous system results in preparation of the body for stressful or emergency situations, while activation of the parasympathetic nervous system results in conservation and restoration and controls body processes during normal situations. For specific organs that are innervated by the autonomic nervous system, it is well known which spinal levels are involved. FIG. 2 shows segmental sympathetic and parasympathetic innervation of various organs. Parasympathetic innervation is either through the vagus nerve (cranial nerve X) or at the sacral levels (S2-S4). Sympathetic pre-ganglionic neurons either synapse in the sympathetic chain ganglia or project through the sympathetic chain ganglia and synapse at various ganglia such as superior mesenteric ganglia or inferior mesenteric ganglia. The post-ganglionic neuron then projects to the end organ that it innervates. Parasympathetic pre-ganglionic neurons (from cranial nerve X and below) synapse very close to the organ they innervate and usually in a nerve plexus attached to the organ, and synapse with a post-ganglionic neuron that sends projections to the organ. The autonomic nervous system includes both sensory and motor neurons.

The ability to activate or inhibit either the sympathetic or parasympathetic nervous system would enable the regulation of numerous bodily functions and enable the treatment of specific disorders related to dysfunction of either the sympathetic or parasympathetic system. Normal functions that are potentially regulated by modulation of sympathetic or parasympathetic activity include modulating bronchodilation in the airways, modulating vasoconstriction in the skin and organs, stimulating gluconeogenesis and glucose release from the liver, stimulating secretion of epinephrine and norepinephrine by the adrenal gland, modulation of sweating, slowing or increasing heartrate and pumping efficiency, modulating tidal volume and rate of respiration, slowing or increasing intestinal processes involved with digestion, modulating urine production, modulating bladder contraction, modulating sphincter control, stimulating erection and sexual arousal, and numerous others. Beyond modulating normal functions, there are numerous disorders of the ANS that have been described and are referred to as dysautonomias, and is due to failure or disruption of either the sympathetic or parasympathetic divisions of the ANS. Specific such disorders include autoimmune autonomic ganglionopathy, congenital central hypoventilation syndrome, familiar dysautonomia, Holmes-Adie syndrome, multiple system atrophy, Shy-Drager syndrome, neurally mediated syncope, orthostatic hypotension, postural tachycardia syndrome, striatonigral degeneration and vasovagal syncope. Elevated sympathetic tone has been linked to disorders such as heart failure, hypertension, obesity, obstructive sleep apnea, diabetes, migraine, parkinsonian symptoms, septic shock, primary hyperhidrosis, complex regional pain syndrome and numerous others.

As there are many disorders and dysfunctions associated with abnormal regulation of autonomically-innervated effector organs, the ability to regulate the autonomic nervous system would enable important new therapeutic strategies. We have developed novel approaches to modulating the autonomic nervous system using various implementations of trans-spinal direct current stimulation (tsDCS).

The bladder is one example of an autonomically controlled organ. The bladder functions as a reservoir and is responsible for storing urine that has been formed by the kidneys in the process of eliminating metabolites and excess water from the blood. The stored urine is released via the urethra in the process of micturition.

The pathways mediating neural control of bladder function are well established and include sympathetic, parasympathetic and somatic pathways. Referring to FIG. 3, sympathetic control of the bladder is from sympathetic efferents from T11-L2 that run via the sympathetic trunk and the splanchnic nerves to the inferior mesenteric ganglion. Post-ganglionic fibers contribute to the hypogastric plexus and reach the bladder where they synapse on the detrusor muscle, and also synapse on the sphincter vesicae at the bladder neck. Parasympathetic control is from parasympathetic fibers that arise from S2-S4 and travel via the pelvic splanchnic nerves to synapse on post-ganglionic neurons located in a dense plexus among the detrusor smooth muscle cells in the wall of the bladder. Post-ganglionic parasympathetic fibers cause contraction of the bladder detrusor muscle and relaxation of the sphincter vesicae. The external urethral sphincter (EUS) consists of striated muscle and is under voluntary control via alpha motor neurons in Onuf's nucleus in the ventral horns of S2-S4. Afferent responses from bladder stretch receptors enter the spinal cord at T11-L2 and also S2-S4 where they travel up to brainstem areas. Sensory fibers in the urethral wall respond to urinary flow by causing firing of their cell bodies located in dorsal root ganglia, which synapse on neurons in the spinal cord dorsal horn. These sensory fibers travel to the spinal cord via the pudendal nerve, and transection of this sensory nerve reduces bladder contraction strength and voiding efficiency.

Urinary retention is an inability to empty the bladder completely and can be acute or chronic. Retention can be due to numerous issues, including constipation, prostatic enlargement, urethral strictures, urinary tract stones, tumors, and nerve conduction problems. Such nerve conduction problems are seen in brain and spinal cord injuries, diabetes, multiple sclerosis, stroke, pelvic surgery, heavy metal poisoning, aging and idiopathically. These result in either weak bladder contraction and/or excess sphincter activation. As such, modulation strategies that enable improved emptying of the bladder are of therapeutic interest.

Urinary incontinence is loss of bladder control leading to mild leaking all the way up to uncontrollable wetting. It results from weak sphincter muscles, overactive bladder muscles, damage to nerves that control the bladder from diseases such as multiple sclerosis and Parkinson's disease, and can occur after prostate surgery. As such, modulation strategies that treat urinary incontinence are of therapeutic interest.

Neurogenic bladder refers to bladder malfunction due to any type of neurological disorder, which can include stroke, multiple sclerosis, spinal cord injury, peripheral nerve lesions and numerous other conditions. Following a stroke, the brain often enters a cerebral shock phase, and the urinary bladder will be in retention (or detrusor areflexia). Around 25% of stroke patients develop acute urinary retention. Following the cerebral shock phase, the bladder often shows detrusor hyperreflexia, and the patient will have urinary frequency, urgency and urge incontinence. In multiple sclerosis, the most common urological dysfunction is detrusor hyperreflexia, occurring in as many as 50-90% of patients with MS. Detrusor areflexia is seen in 20-30% of patients, so treatment must be individualized based on urodynamic findings. In spinal cord injuries occurring from motor vehicle or diving accidents, an initial response of spinal shock is seen in which patients experience flaccid paralysis below the level of injury, and experiences urinary retention consistent with detrusor areflexia. Spinal shock phase lasts usually 6-12 weeks but may be prolonged. During this period, the urinary bladder often must be drained with either intermittent catheterization or an indwelling catheter. Following the spinal shock phase, bladder function returns, however with an increase in excitability, and results in detrusor hyperreflexia. Peripheral nerve lesions can be due to diabetes mellitus, herpes zoster, neurosyphilis, herniated lumbar disk disease, pelvic surgery and other conditions, and can result in detrusor areflexia. There is a continuing and unmet need for improved ability to impose beneficial control over behavior of end effectors. Embodiments of the present invention are variously directed to meeting such need.

SUMMARY OF THE INVENTION

As there are many disorders and dysfunctions related to the nervous system, such as those associated with abnormal regulation of autonomically-innervated effector organs, the ability to regulate related parts of the nervous system, such as the autonomic nervous system, enables new therapeutic strategies and interventions. We disclose novel systems, devices, apparatuses and methods for modulating parts of the nervous systems using various implementations of trans-spinal direct current stimulation (tsDCS) and we provide new therapeutic strategies and interventions for modulation of bladder and other organs using trans-spinal direct current stimulation.

Therefore the present invention relates to methods and systems utilizing trans-spinal direct current stimulation for modulation of target effector organs. Illustrative embodiments of this disclosure are directed to application of tsDCS to modulation of effector constituents of the autonomic nervous system (ANS), and illustrative embodiments include method and apparatus for treatment of bladder dysfunctions. Such disclosure is by way of illustration and not by way of limitation of the scope of the present invention to other organs.

We apply tsDCS in various configurations. In some embodiments, we use tsDCS by itself. In other embodiments, we use coordinated multi-site neurostimulation that incorporates tsDCS together with stimulation at other site(s) along the neural axis.

In a double-stimulation configuration, we provide simultaneous spinal tsDCS stimulation together with a second stimulation. In one embodiment we provide tsDCS spinal stimulation combined with direct current peripheral stimulation of a nerve leading to a targeted effector organ. In an alternative double-stimulation configuration, we provide simultaneous spinal stimulation together with a second stimulation that modulates central autonomic outflow.

In a triple-stimulation configuration, we provide simultaneous stimulation of cerebral, spinal and peripheral sites serving target effector organs, e.g., organs such as the bladder or external urethral sphincter (EUS). Through such coordinated multi-site neurostimulation, the descending cortical signals are amplified by spinal-level tsDCS to drive stronger responses at the target effector organ. This approach effectively stimulates neural pathways and enables delivery of stronger cortical signals to drive stronger effector responses.

In one embodiment, method and system for modulating function of the autonomic nervous system in a vertebrate being is provided, including a primary stimulation component which initiates central autonomic outflow, and a second stimulation component which modulates descending autonomic pathways at the level of the spinal cord. A further embodiment includes a primary stimulation component that includes either transcranial direct current stimulation, transcutaneous vagal nerve stimulation, transcranial magnetic stimulation, cold/hot pressors, oral or transdermal pharmaceutical agents, visual stimuli, auditory stimuli, olfactory stimuli or other forms of stimulation. In some embodiments, the secondary stimulation component comprises trans-spinal direct current stimulation and the autonomic outflow is either sympathetic outflow or parasympathetic outflow.

A further method and system for modulating function of the autonomic nervous system in a vertebrate being is provided, including a primary stimulation component which initiates central autonomic outflow, a second stimulation component which modulates descending autonomic pathways at the level of the spinal cord, and a third peripheral stimulation component which stimulates a nerve leading to a target effector organ.

In embodiments of the invention we incorporate a wearable tsDCS controller that modulates descending autonomic signals traversing the spinal cord. In some embodiments, this is combined with an implanted electrode that directly stimulates the nerve to a targeted effector organ. The implanted electrode is in wireless communication with the wearable tsDCS controller. This stimulation is selected as either excitatory or inhibitory in practices of the invention.

This approach is sufficient for certain applications. In other applications, it is beneficial to directly modulate central autonomic outflow before spinal level modulation via tsDCS. In several practices of the invention, we increase or decrease sympathetic outflow, or increase or decrease parasympathetic outflow. Furthermore, in particular embodiments we provide non-invasive and non-pharmacological modulation of autonomic outflow for control and treatment of autonomically-related functions and disorders. In other embodiments, we provide pharmacological modulation of autonomic outflow for control and treatment of autonomically-related functions and disorders.

We apply tsDCS in various configurations. In embodiments of the invention, the stimulation applied to the spine is a continuous constant current direct current signal. For practical reasons, this constant tsDCS signal is ramped at the beginning and end of application to reduce local induced stimulation artifacts. In some embodiments this is a pulsed signal which delivers an equivalent continuous constant-current signal to the stimulation site.

In various embodiments, the tsDCS spinal stimulation is applied with an active electrode at the spine being driven as either anode or cathode and cooperating with its complimentary return electrode to define the spinal circuit. The distal neural stimulation, sometimes referred to as peripheral direct current stimulation (pDCS) is applied with the distal active electrode at a nerve to the target effector organ being driven as either anode or cathode at the opposite polarity of the active spinal electrode, and also cooperating with the distal complementary return electrode to define the distal peripheral circuit between these electrodes. These spinal and peripheral stimulation circuits are energized and during such energized state create a resulting circuit between the active spinal electrode and the active neural electrode. This forms an active resulting anode-cathode pair, with the resulting current flow between this energized pair during the stimulation period favorably polarizing the connecting neural pathway down to the nerve at target effector organ. The result of applying such stimulation is to modulate neural transmission from spinal cord to the target effector organ, resulting in modulation of function at the target effector organ.

BRIEF DESCRIPTION OF THE DRAWINGS

The above illustrative and further embodiments are described below in conjunction with the following drawings, where specifically numbered components are described and will be appreciated to be thus described in all figures of the disclosure:

FIG. 2: shows segmental sympathetic and parasympathetic innervation of various organs;

FIG. 4A: shows illustrative stimulator devices in practice of embodiments of the invention;

FIG. 4B: shows common TMS magnetic stimulator with figure-eight probe in practice of embodiments of the invention;

FIG. 6: shows surgical placement of cysostomy tube into the bladder to enable measurement of bladder pressures and urine output, in practice of embodiments of the invention;

DETAILED DESCRIPTION OF THE INVENTION

Figure 1:
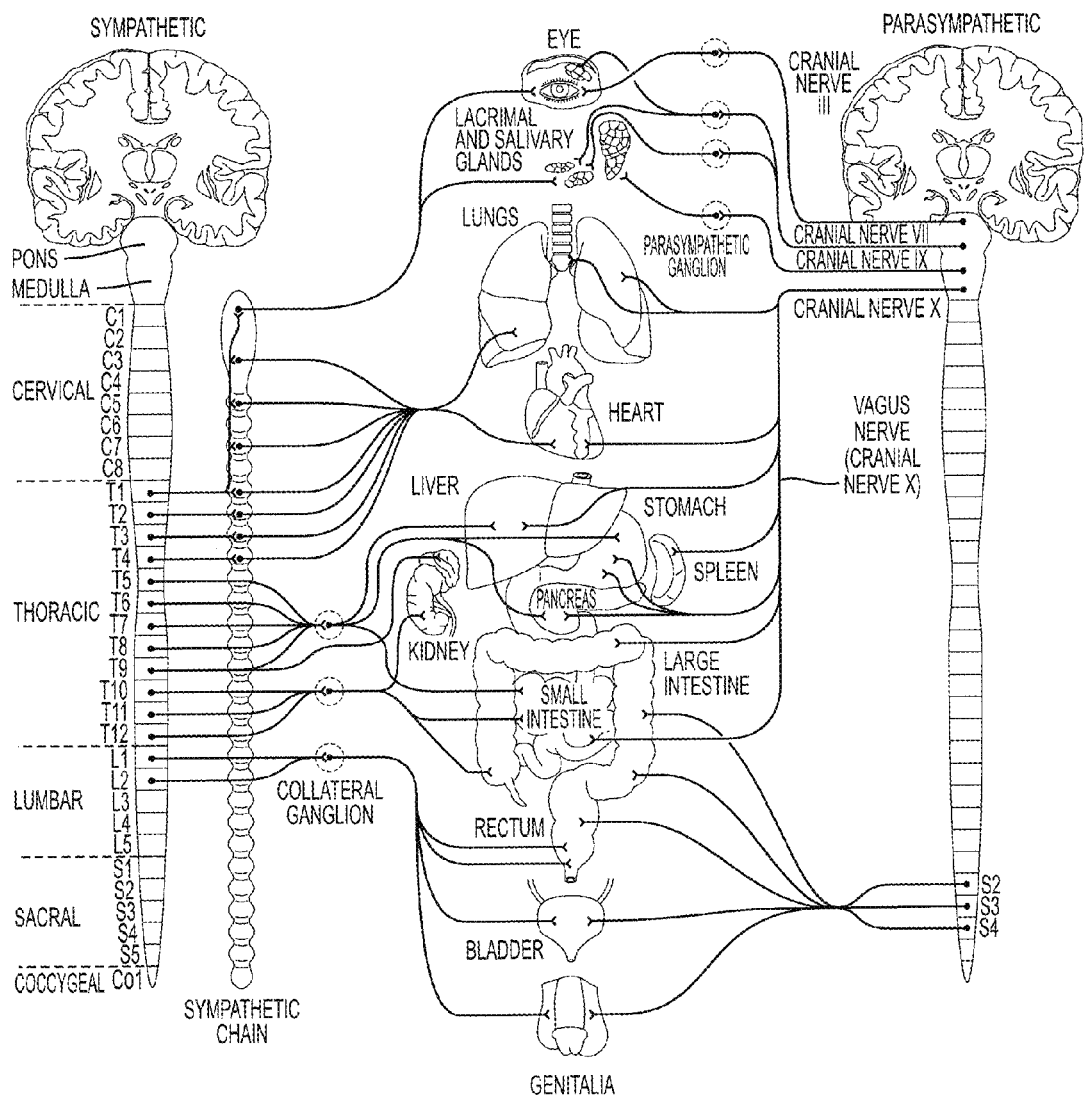
FIG. 1 shows the two divisions of the Autonomic Nervous System: the sympathetic nervous system and the parasympathetic nervous system.
Figure 3:
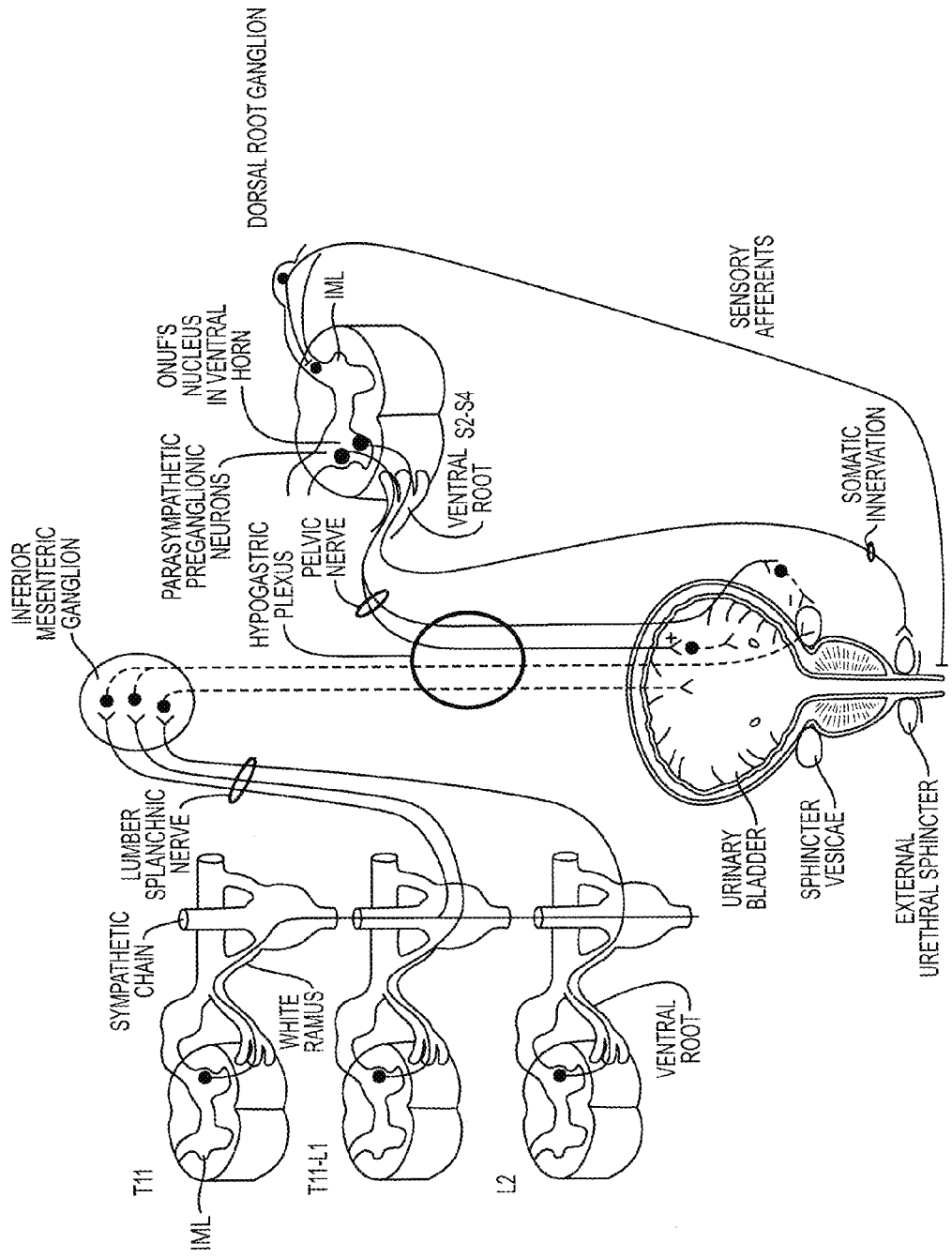
FIG. 3: shows well-known pathways mediating neural control of bladder function.

The description is not to be taken in a limiting sense, but is made merely for the purpose of illustrating the general principles of these teachings, since the scope of these teachings is best defined by the appended claims.

As used herein, the singular forms "a," "an," and "the" include the plural reference unless the context clearly dictates otherwise.

The following definitions pertain to the present disclosure, with the understanding that such may be modified by context of use. For purposes of the teaching of the present teachings:

The term "nerves" may be referred to herein as including nerves, neurons, motor neurons and interneurons and the like, and are generally referred to herein as "nerves" or "neurons";

The terms or concepts of nerve stimulation and neural stimulation are used liberally and interchangeably to describe applications of the stimulation of the teachings;

The terms neuromodulation, modulation, stimulation and regulation are used interchangeably as equivalents for purposes of this disclosure and indicate an effect imposed upon a target in practice of present teachings;

The terms dysfunction, disorder, defect and abnormality are used interchangeably as equivalents for purposes of this disclosure and indicate the concept of medically recognized conditions suitable for medical intervention:

The term effector organ refers to a neurally-innervated organ that produces an effect in response to nerve stimulation. Muscles are included within such definition for purposes of this disclosure. The effects of stimulation of the present teachings upon an effector organ or muscle may be discussed interchangeably for purposes of inclusive discussion of the present teachings.

The term "stimulation," as used herein, refers to either excitation or inhibition of nerve fibers, also referred to as up regulation or down regulation.

The term "electrical stimulation," as used herein refers to the production or introduction of current into spinal nerve, neuron, circuit or pathway, whether by applying a voltage or magnetically inducing a current.

Improved method and apparatus for neuromodulation and regulation of effector organs are disclosed herein below.

In practice of embodiments of the invention, we provide benchtop, wearable or implantable systems for modulating the components of the nervous system, including effector organs. Strategies that provide spinal stimulation via tsDCS (mono-stimulation), spinal stimulation via tsDCS combined with either peripheral stimulation or stimulation of central autonomic outflow (double-stimulation), and spinal stimulation via tsDCS combined with peripheral stimulation and stimulation of cortex (e.g., motor cortex) or central autonomic outflow (triple-stimulation), are disclosed. In illustrative embodiments herein, we disclose methods and apparatus that apply these strategies to modulate the autonomic nervous system and to regulate autonomically-innervated effector organs such as the bladder. These strategies treat nervous system conditions, including bladder incontinence and bladder retention.

In practice of embodiments of the invention, we provide benchtop, wearable or implantable systems for modulating the components of the nervous system, including effector organs. Strategies provide spinal stimulation by applying tsDCS on its own (mono-stimulation), or tsDCS spinal stimulation combined with peripheral stimulation (double-stimulation), or tsDCS spinal stimulation combined with cerebral stimulation (double-stimulation), or tsDCS spinal stimulation combined with two other stimulations, which may include peripheral stimulation and cerebral stimulation (triple-stimulation), are disclosed. In illustrative embodiments herein, we disclose methods and apparatus that apply these strategies to modulate the autonomic nervous system and to regulate autonomically-innervated effector organs such as, but not limited to, the bladder. These strategies treat nervous system conditions, including bladder incontinence and bladder retention.

FIG. 4A shows illustrative stimulator devices 10,12, 14 which may be utilized in various practices of the invention. These devices include a tsDCS stimulation device 10 which may be used on its own to deliver a tsDCS mono-stimulation treatment or in combination with additional stimulation devices 12 and/or 14 to provide various double and triple stimulation treatments, in several embodiments of the invention.

tsDCS stimulator device 10 delivers trans-spinal direct current stimulation to a spinal location neurally associated with a distal effector organ of interest, and more particularly associated with function of a target effector organ, such as the bladder. In various embodiments the stimulation supplied by stimulator device 10 provides monopolar, and an essentially or effectively continuous, constant, non-varying direct current stimulation of a selected polarity, in a range of 0.5 to 5 or 6 mA, typically 1-4.5 mA. Stimulator device 10 illustrates a tsDCS component in embodiments of the invention. In this illustration, device 10 includes a computing and synchronizing unit 16, for provision of a system control function, and including a signal polarity and function controller 18, and having a system memory 19. The second stimulator device 12 provides a known transcranial direct current (tDCS) stimulation source of pulsed or constant direct current stimulation to the cortex area C, having a circuit 20 for signal computing and synchronizing, and for control of signal polarity and function, integrated with resident memory 19. In an alternative embodiment, repetitive pulsed magnetic stimulation (rTMS) is provided to the cortical area C by a TMS magnetic stimulator 12A using a figure-eight probe 22, as shown in FIG. 4B, as will be understood by a person skilled in the art.

In an illustrative embodiment, pulsed electrical stimulation of the motor cortex in an adult ranges at 100-400 mA, typically around 200 mA, pulse width of 100-300 microseconds, typically around 200 ms, 0.5 to 3 Hz repetition rate, operating voltage 400-800. For a child, 70-100 milliamps at 100 microseconds is a target. Magnetic stimulation is alternatively applied, and in an illustrative pulsed TMS embodiment, magnetic stimulation is delivered at a rate of 0.5 to 3 Hz, 200 microsecond pulse width, reaching stimulation current levels equivalent to the electrical stimulation, as will be understood by a person skilled in the art. In one TMS practice of the invention, rTMS is applied with a magnetic flux density of 1.0 to 1.5 Tesla.

The third stimulator device 14 is a source of direct current stimulation to stimulate a peripheral location of interest, typically for stimulation of a nerve leading to a target effector organ of interest, such as the bladder, and which may include non-varying or pulsed direct current stimulation. This stimulator device 14 includes a circuit 23 for signal computing and synchronizing and for control of signal polarity and function, with resident memory. An illustrative peripheral constant direct current stimulation is applied at levels of 1-5 mA for double stimulation and with pulsed peripheral intensity typically ranges is from 5 to 40 mA for triple stimulation. In a bladder treatment of the invention, continuous tsDCS is applied to the Onuf's nucleus in the sacral region of the spinal cord, with typical intensity in the range from 1-4.5 mA.

All three of devices 10, 14, 12, are shown having an I/O component for external signal connection, such as with electrodes, 24, 26, 30, 32, and 34, 36, respectively, providing +/− terminals for electrode connection. Each unit is also provided with a communication component 40, which enables data links 42 for wired or wireless communication between the devices or with other external devices. In this illustration, all three devices 10, 12, 14 have a user interface with microprocessor unit 44 and a power supply P, such as rechargeable batteries.

The tsDCS stimulator device 10 is engaged on its own when tsDCS mono-stimulation is provided. For double stimulation, the tsDCS stimulator device 10 is engaged along with another stimulation source, such as provided by the cortical stimulator device 12 in one practice or by the peripheral stimulator device 14 in another practice of the invention. In one practice double-stimulation is provided by two independent or isolated circuits with the same or paired stimulation devices.

As will be appreciated by a person skilled in the art, in several embodiments, where constant current stimulation is to be delivered to the patient, the two cooperating stimulation sources, such as devices 10 and 14 share a common ground in order to enable an efficient control function as the circuits attempt to maintain assigned signal levels over time in the presence of changing resistance of the current path(s) within the patient.

In some embodiments, the tsDCS stimulator device 10 is engaged to provide tsDCS in a triple-stimulation embodiment, in cooperation with other two stimulation sources, such as with the cortical stimulator device 12 and the peripheral stimulator device 14. In an illustrative embodiment, the tsDCS triple-stimulation includes pulsed stimulation at the cortex, constant stimulation at the spine and pulsed stimulation at the peripheral location.

Referring to FIG. 4A, a person to be treated is shown from the back. Three sets of electrode connections are shown as would be used during an illustrative triple stimulation practice of the invention. Electrodes will be applied in locations discussed below.

As an illustration only, in a tsDCS triple stimulation embodiment, the cortical stimulator 12 provides transcortical direct current (tDCS) stimulation as a source of direct current to the local cortical area C via active cortical electrode 34 and return (also called "reference") electrode 36. The stimulation path 34-36 is defined between the two electrodes to stimulate the local cortex area C which is associated with the intended stimulation of a target effector organ of interest, such as bladder 21 (indicated by dotted symbol). In an alternative embodiment, repetitive pulsed magnetic stimulation (rTMS) is supplied to cortical area C by a probe 22 of a TMS magnetic stimulator 12A shown in FIG. 4B, for application of known pulsed cortical stimulation, as will be understood by a person skilled in the art.

The tsDCS stimulator 10 delivers trans-spinal direct current mono-stimulation to a spinal location 15 associated with neural outflow associated with a target effector organ, such as at the bladder. The spinal active electrode 24 is applied at spinal location 15 and a return electrode 26 is located distal to the spinal area, such as at an anterior aspect of the body. In this embodiment, a spinal stimulation circuit 17 is defined between these two electrodes with the stimulation current traversing the spinal processes at that location as a stimulation path of interest.

The third stimulator 14 provides peripheral direct current stimulation to stimulate a nerve leading to a target effector organ or a nerve of the target effector organ, such as the bladder 21. In one embodiment, the stimulation signal is monopolar and pulsed. In another embodiment the stimulation signal is monopolar and constant.

An illustrative embodiment of the invention includes method and system having a single tsDCS stimulation circuit, for mono-stimulation of the spinal cord, and defined by placing an electrode at the spinal location of interest and a return electrode on the anterior aspect of the body, thus defining a pathway of interest between these electrodes. In various practices of the invention, these electrodes are assigned as either anode or cathode and a tsDCS stimulation circuit is thus created for applying current between the electrodes and for modulating spinal cord excitability. The applied current is delivered having a desired signal character and level. In further embodiments of the invention, we apply these teachings in wearable and implantable embodiments.

In a further embodiment of the invention, a wearable mono-stimulation device is provided. In this practice, there are two electrodes which are skin surface type, serving as the active spinal electrode and the spinal circuit return electrode. In one embodiment, a surface of the wearable device provides the spinal electrode and the device also connects to a return electrode, on the opposite side of the spinal cord, which is placed on the skin surface such as on the abdomen or iliac crest. In another embodiment, the reference electrode is placed internal to the bladder, such as by urethral catheter insertion, surgically, or the like. The spinal location of interest is selected based on spinal outflow to the target effector organ. In another implantable mono-stimulation device of the invention, there are two electrodes which are implantable electrodes, serving as the active spinal electrode and the return electrode. In one embodiment, the mono-stimulation device is fully implantable, with electrode leads from the device to dorsal spinal location and ventral location tunneled subcutaneously. The spinal location of interest is selected based on spinal outflow to the target effector organ.

In a fully implantable subcutaneous double-stimulation embodiment of the invention, two circuits are supplied by four leads emanating from controller device. This embodiment delivers two simultaneous stimulations, a spinal stimulation and a peripheral stimulation applied to a nerve of the target effector organ. There are two separate stimulation current paths with these two circuits. But these circuits also interact to form a resulting stimulation current path between the active electrode at the spine of the spinal circuit and the electrode of opposite polarity positioned at the nerve of the target effector organ. This provides a polarization flow down along the neural path between the two described electrodes. In this double stimulation embodiment, the first current path is a tsDCS spinal circuit defined by placing an active spinal electrode at the spinal location of interest and a return electrode at a non-spinal location, with the applied current running between these electrodes. The second current path is a peripheral circuit defined by placing active and return electrodes on or in proximity to a nerve of the target effector organ.

In a further embodiment, a two-part semi-implantable stimulation device is provided. A first component is a wearable mono-stimulation device which includes an active spinal electrode applied by skin attachment and a return electrode. The second component is an implanted peripheral stimulator or microstimulator with two leads that has its own power supply. Both leads of the second component are in contact with or in close proximity to a nerve of a target effector organ. The wearable component can communicate wirelessly with the implanted component. When the wearable component turns on and issues its stimulation signal, the implanted stimulator responds and issues a stimulation signal to the target effector organ, which can be either excitatory or inhibitory.

In a further embodiment of a wearable double-stimulation device, two circuits are supplied by four leads emanating from controller device. This embodiment delivers two simultaneous stimulations. The first stimulation is a spinal stimulation delivered via active spinal electrode applied by skin attachment and a return electrode. The second stimulation modulates central autonomic outflow, and can be either trans-cranial direct current stimulation (tDCS) or trans-cutaneous vagal nerve stimulation (tVNS). There are two separate stimulation current paths with these two circuits but they are electrically isolated from each other.

In a further embodiment, a two-part semi-implantable stimulation device is provided. A first component is a wearable double-stimulation device that provides a first stimulation that is spinal stimulation, and a second stimulation that modulates central autonomic outflow. The second component is an implanted peripheral stimulator or microstimulator with two leads that has its own power supply. Both leads of the second component are in contact with or in close proximity to a nerve of a target effector organ. The wearable component can communicate wirelessly with the implanted component. When the wearable component turns on and issues its stimulation signal, the implanted stimulator responds and issues a stimulation signal to the target effector organ, which can be either excitatory or inhibitory.

Figure 5A:
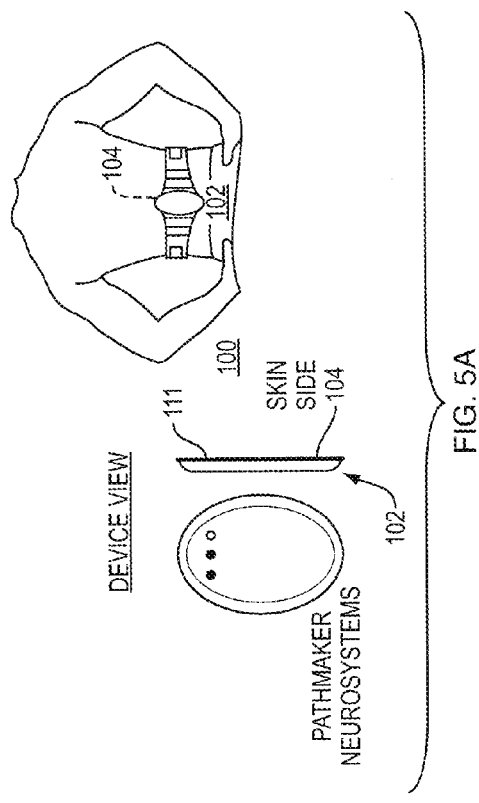
FIGS. 5A-C: show illustrative wearable and implantable components and configurations, including a closed-loop system, in practice of embodiments of the invention.
Figure 5B:
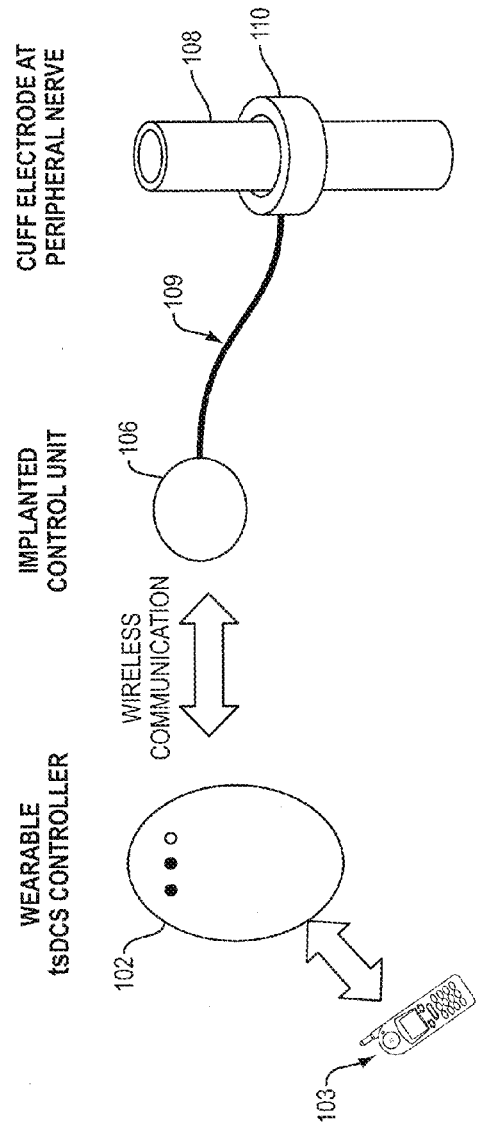
Figure 5C:
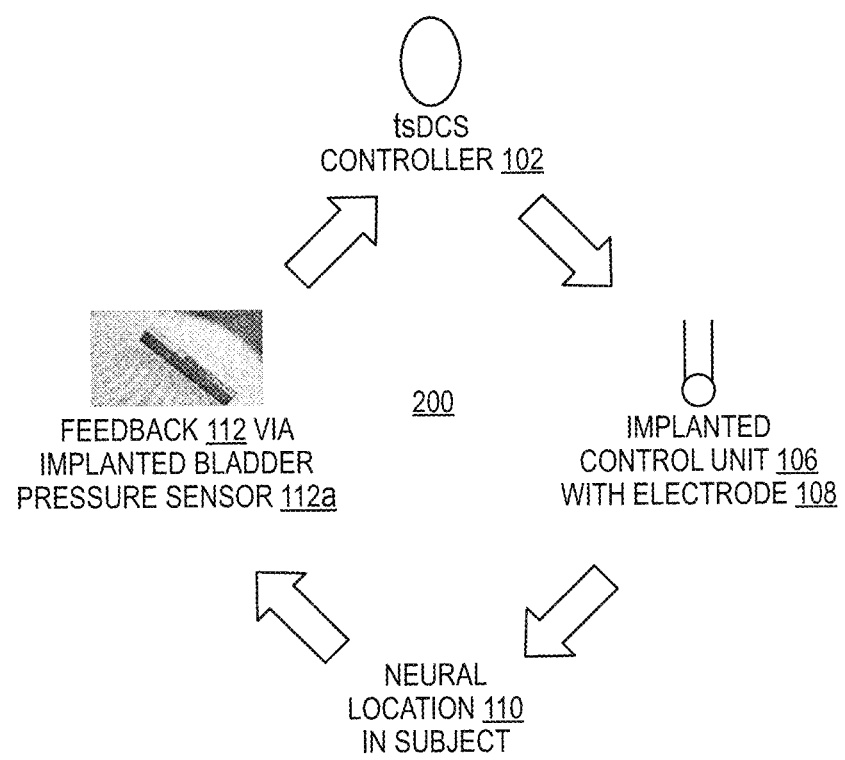

Illustrative embodiments of the invention is set forth in FIG. 5A-C featuring wearable and implantable components.

In FIG. 5A, a disk-shaped wearable system 100 is disclosed. As illustrated in FIG. 5A-B, system 100 includes a wearable/implantable tsDCS controller 102, shown affixed to the patient at its skin-side 104 optionally presenting an electrode surface 111. External interaction with controller 102 is by buttons or touch screen or by wireless interaction with a portable device or cell phone 103 for user intervention. Controller 102 directs action of implanted control unit 106.

Controller 102 incorporates a cognate circuit of device 10, FIG. 4A, including a miniaturized version of computing and synchronizing unit 16, with memory 19, for provision of system control, and further including a signal polarity and function controller 18, with appropriate instruction loaded set in memory 19 for instruction of implanted control unit 106. Control unit 106 includes a rechargeable power supply (not shown), and according to instructions from controller 102, applies electrical stimulation to a local peripheral nerve 108 that innervates a target effector organ, such as the bladder. The stimulation can be adjusted as needed, and is provided as constant continuous non-varying direct current stimulation, or can be pulsed direct current stimulation, in various practices of the invention.

In one embodiment, the implanted control unit 106 provides electrical leads 109 to deliver the stimulation signal to suitable electrode, shown as a cuff electrode 110, which is affixed at nerve 108. In one embodiment, controller 102 presents an electrode surface 111 on the skin side of the device for affixation of the device to the patient. This electrode surface 111 may include electrically conductive adhesive to assist attachment to the patient, and permits application of tsDCS stimulation at that location. In further embodiments of the invention, system 100 further includes and cooperates with the implanted control unit 106, which in turn drives single or multiple implanted electrodes, such as a cuff electrode 110 via leads 109. Cuff electrode 110 is placed around a peripheral or autonomic nerve of interest 108 and stimulates the nerve fibers to achieve either excitation or inhibition of the effector organ, e.g., bladder. The cuff electrode 110 is made of soft, flexible materials such as silicone that render an electrode flexible and less prone to injure the peripheral nerve than common electrodes. Alternatively, two electrode leads representing the anode and cathode are positioned in contact with or in close proximity to the nerve 108.

In another embodiment of the present teachings, a wearable tsDCS unit that wirelessly controls an implanted stimulator is combined with a sensor that detects a relevant physiological state to form a closed-loop system. The wearable tsDCS unit wirelessly communicates with the sensor, which could be either implanted or wearable, and activates tsDCS spinal stimulation and stimulation of an effector organ via the implanted stimulator, when it detects a relevant state. The sensor can be configured to detect blood pressure, heart rate, body temperature, respiration rate, skin turgor, skin conductivity, oxygenation state, bladder pressure, urine osmolarity, hemodynamic parameters, specific cardiac rhythms by EKG, urethral pressure, anal sphincter pressure, muscle contraction state by EMG, specific brain waves by EEG, electrolytes, specific proteins and signaling molecules in specific tissue compartments, blood glucose concentration, gastric pH, gastrointestinal motility sounds, environmental cues such as specific sights, sounds and signals, and other parameters depending on intended application. The neuromodulation system is thus activated upon sensing a specific state, and inactivated when that state no longer holds. In one embodiment of the present teachings, the system also includes a sensor configured to detect a predetermined parameter, such as those listed herein above, and configured to provide a sensed value of the predetermined parameter to the controller component. The controller component is further configured to initiate stimulation, initiation of stimulation determined by whether the sensed value is less than or exceeds a predetermined value denoting the specific state.

A closed loop system 200 of the invention is shown in FIG. 5C and is configured to operate autonomously in the background with reduced user interaction. As will be appreciated by a person skilled in the art, the system 200 takes advantage of modern wireless communications, as shown, which is available to implanted medical systems. System 200 includes tsDCS controller 102 and implanted control unit 106 with implanted electrode 110 at nerve 108, and including an implanted feedback device 112. The feedback device 112 is in wireless communication with controller 102, which then responsively instructs control unit 106 to adjust or initiate or cease the stimulation function as needed.

The implanted stimulator, control unit 106, stimulates nerve 108 via leads 109 and electrode 110, consistent with instructions from controller 102.

In a bladder management embodiment, the implanted feedback device 112 is a bladder pressure sensor 112A. Bladder data from sensor 112A is wirelessly provided to controller 102 which wirelessly instructs implanted control unit 106, or directly instructs control unit 106, to control stimulation of bladder nerve 108 via electrode 110, to reduce incontinence or to reduce urinary retention, for example.

Controller unit 102 has human interface, common instruction memory store, and logic circuits, and or a microprocessor, for executing its control instructions to control unit 106. In turn, the control unit has a power supply which supplies the electrode accordingly. Preferably the power supply is wirelessly rechargeable.

The implanted sensor 112A closes the loop with the device controller circuit 102 in system 200 such that the system automatically adjusts without user intervention, according to stored profiles. In one embodiment of bladder modulation, the implanted sensor 112A is a bladder function sensor such as a bladder pressure sensor which detects bladder pressure exerted by urine volume in the bladder and enables and wirelessly informs the needed neural stimulation instruction to be issued from controller 102 to control unit 106 to initiate stimulation and to obtain a desired outcome, such as controlled voiding. In one embodiment, the data from bladder sensor 112A is directly acted upon by control unit 106.

In a further application of the closed-loop system 200 of FIG. 5C, we combine stimulation that modulates central autonomic outflow, in which a primary stimulation modulates either the sympathetic or parasympathetic branch of the autonomic nervous system, with the closed-loop system 200. Thus, cerebral and spinal stimulations are combined with an implanted stimulator that is under the control of the wearable tsDCS controller.

It will be appreciated that embodiments of the present teachings feature tsDCS spinal stimulation. In many embodiments, this tsDCS stimulation is augmented with stimulation of a peripheral nerve leading to a target effector organ. In practices of these teachings, peripheral direct current stimulation (pDCS) is continuous, non-varying, steady-state direct current stimulation, while in other embodiments, stimulation of a peripheral nerve or autonomic nerve fiber associated with an effector organ may include pulsed electrical stimulation, continuous DCS, pulsed DCS, or other alternating signals. The present teachings also may be practiced with wireless microstimulators as known in the art.

In practice of the invention, we apply tsDCS in various configurations. A tsDCS stimulation system provides tsDCS stimulation, which in various embodiments is applied by itself to favorably polarize a target neural pathway of interest. In other embodiments, we use coordinated multi-site neurostimulation that incorporates the tsDCS polarizing stimulation together with stimulation at other site(s) along the neural axis. We provide this multi-site stimulation by combination of tsDCS stimulation with at least one other stimulation, which includes cerebral stimulation and/or peripheral stimulation.

In one embodiment of the present teachings, peripheral stimulation is continuous steady-state and non-varying. In another embodiment of the invention, excitation or inhibition of a stimulated autonomic nerve fiber depends on the frequency of the applied electrical stimulation. In one illustrative but non-limiting practice of the invention, inhibition of parasympathetic fibers is achieved with high-frequency monopolar electrical stimulation (greater than about 50-100 Hz), while excitation of parasympathetic fibers is achieved with low-frequency monopolar electrical stimulation (less than about 50-100 Hz). Similarly, inhibition of sympathetic fibers is achieved with high-frequency electrical stimulation (greater than about 50-100 Hz), while excitation of sympathetic fibers is achieved with low-frequency electrical stimulation (less than about 50-100 Hz). In various embodiments we apply stimulation via skin surface electrodes in a range up to about 1-6 mA or more often at 1-4.5 mA.

In embodiments of the present teachings, the tsDCS device is fully implantable, with electrode leads from the device to dorsal spinal location and ventral location tunneled subcutaneously. Electrode leads from the tsDCS device which function for peripheral stimulation are also tunneled subcutaneously with electrodes implanted on the appropriate nerves of the effector organ being modulated. In another embodiment, the tsDCS device remains external to the body and wearable, but has electrode leads for peripheral stimulation that are either surface mounted or implanted.

Illustrative Mono-Stimulation Embodiments

It will be appreciated that the mono-stimulation process involves applying a single source of constant current stimulation and is typically delivered by the tsDCS stimulator alone. In practice of the present invention, we employ tsDCS to induce either an area of increased or decreased neural activation within the spinal cord.

The present invention teaches methods and systems utilizing trans-spinal direct current stimulation for modulation of body functions, such as at effector organs. Illustrative embodiments of this disclosure are directed to application of such tsDCS to modulation of effector constituents of the autonomic nervous system (ANS). Illustrative embodiments include method and apparatus for treatment of bladder dysfunctions. This disclosure is by way of illustration and not by way of limitation of the scope of the present invention.

It will now be appreciated that in various practices of the invention, tsDCS stimulation is applied at the spinal location. At peripheral sites (or cerebral sites in the case of transcutaneous vagus nerve stimulation), stimulation can be of a broader variety within the scope of the invention. In several practices of the present invention, monopolar direct current stimulation is applied at specific points along the neural axis. Monopolar direct current electrical stimulation is applied and characterized as anodal or cathodal. In an embodiment of the invention, this characterization is indicative of the polarity of the current source as applied between a spinal location of interest and a return location. Depending upon the desired outcome, the circuit may be applied as anodal, positive, at the location of interest, and cathodal, negative, at the return location, or vice versa.

Single and/or multiple monopolar direct current stimulation circuits are engaged in various embodiments. These monopolar stimulations are, characterized as being anodal or cathodal, have a polarizing effect over the stimulated pathways. This polarization has significant favorable modulatory effect upon the transmission efficiency of neural signals flowing over a neural pathway of interest. Monopolar stimulation applied to a neural pathway has potential polarizing and modulatory affects. In various practices of the invention, we engage and harness these effects accordingly.

Figure 7A:
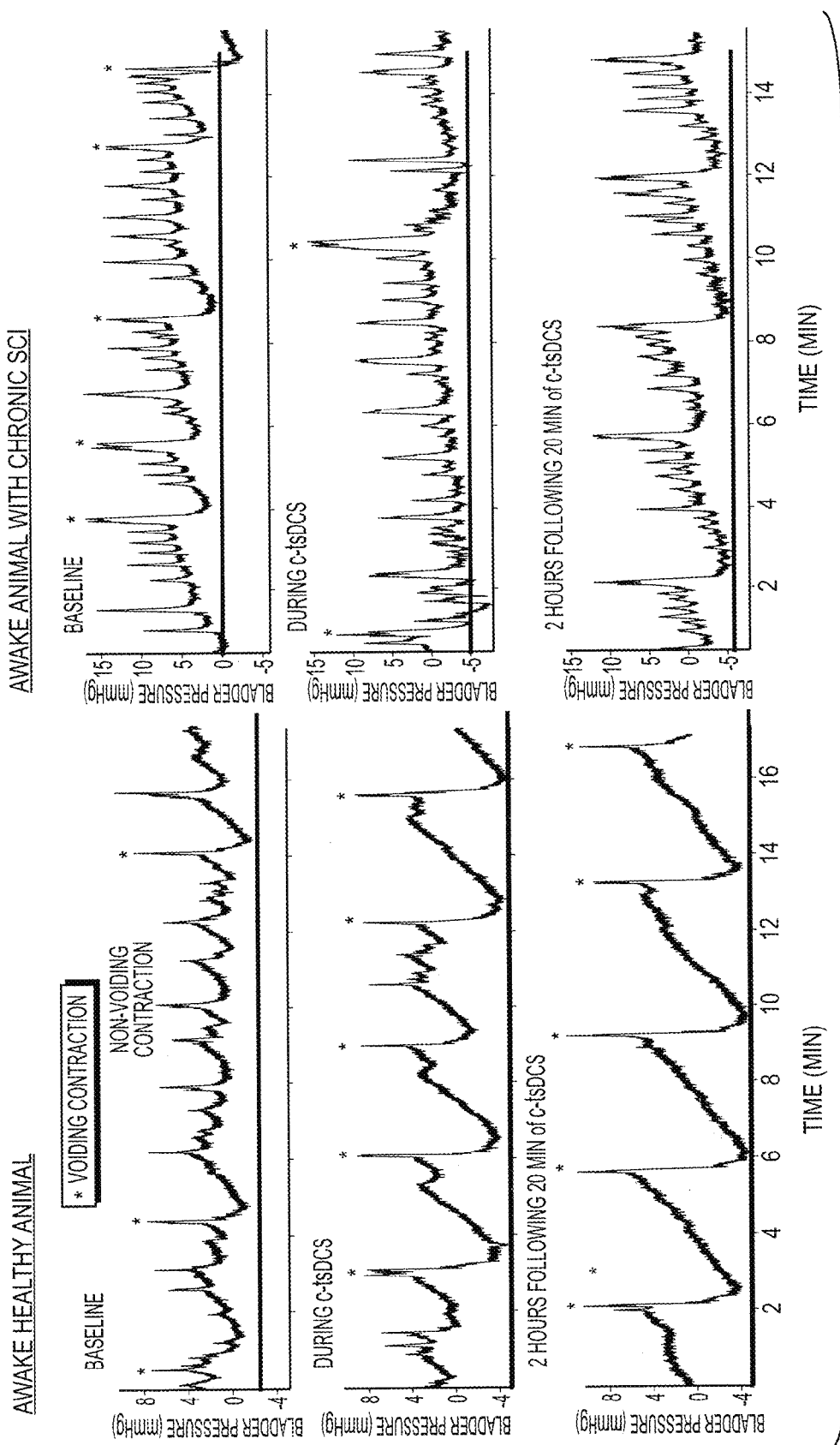
FIG. 7A: shows bladder pressures and the frequency of voiding and non-voiding contractions measured at baseline prior to stimulation with cathodal tsDCS, in practice of embodiments of the invention.

In an illustrative embodiment of the invention in awake healthy mice, a two-electrode mono-stimulation configuration of tsDCS was utilized, employing a stimulator, with an active cathode electrode on the lumbosacral spine (L6-S3), and a return anode electrode on the abdomen. To enable measurements of bladder function, we surgically placed a cysostomy tube (PESO tubing) into the bladder to enable measurement of bladder pressures and urine output (FIG. 6). Bladder pressures, and the frequency of voiding and non-voiding contractions were measured at baseline prior to stimulation with cathodal tsDCS (FIG. 7A). In such embodiments with cathodal tsDCS providing stimulation, there is a decrease in the basal pressure, increase in the amplitude of bladder contractions, increase in inter-voiding contraction interval, and increase the number and amplitude of non-voiding contractions. In a series of experiments, after 20 minutes of cathodal tsDCS, these effects were still apparent. With such stimulation, the bladder can contract more fully.

The same stimulation paradigm was also evaluated in awake mice with chronic spinal cord injury, with spinal cord lesioning at T10 level 30 days prior to stimulation studies. In these subjects, there is excessive bladder activity and non-voiding contractions, with higher bladder pressures as compared to healthy subjects, a condition of detrusor hyperreflexia. Baseline measurements were done in these subjects, followed by measurements during cathodal tsDCS, and 2 hours after 20 minutes of cathodal tsDCS. In awake subjects with chronic spinal cord injury, there is a decrease in the basal pressure, larger non-voiding contractions, and a decreased frequency of voiding contractions. Similar to awake healthy subjects, cathodal tsDCS enables the bladder of subjects with chronic spinal cord injury to contract more fully.

Figure 7B:
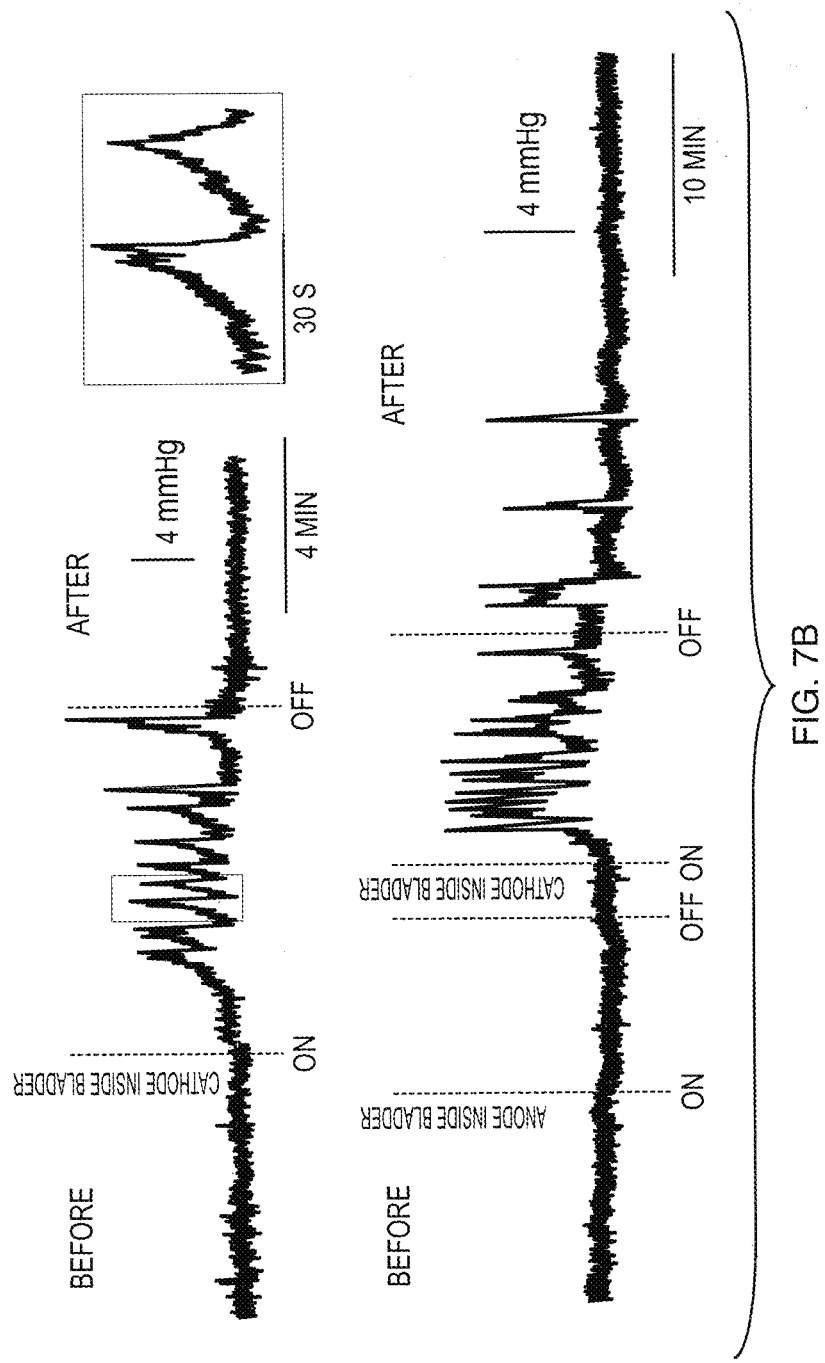
FIG. 7B: shows spinal to bladder tsDCS stimulation that initiated bladder retention and voiding reflex in a vertebrate being with severe chronic spinal cord injury, in practice of embodiments of the invention.

In another embodiment relating to treatment of chronic spinal cord injury in mice, a two-electrode configuration of tsDCS was utilized, with an anodal electrode on the lumbosacral spine (L6-S3), and with, in one embodiment, the return electrode on the front of the subject's abdomen, and in another embodiment, with the return electrode at the bladder wall via transurethral insertion. FIG. 7B shows spinal to bladder tsDCS stimulation that initiated bladder retention and voiding reflex in a vertebrate being with severe chronic spinal cord injury. The subject had demonstrated skin irritation caused by excessive urination due to inability to retain urine. The top provides cystometry traces showing intravesicle pressure before, during, and after stimulation with anode on the spine and cathode inside the bladder. Note that there were no reflexes before or after stimulation. Traces on the right are with expanded time scale to show the structure of the reflexes. The bottom trace shows cystometry traces from the same subject showing before, during stimulation 1 (anode inside the bladder), stimulation 2 (cathode inside the bladder), and after. An improved ability to retain urine is seen even after stimulation is switched off.

In further studies of mice with acute spinal cord injury, the same two-electrode configuration of tsDCS was utilized. In acute spinal cord injury, there is spinal shock and detrusor areflexia, during which period the bladder fills to high and potentially dangerous pressures, with voiding pressures significantly higher than normal subjects or in subjects with chronic spinal cord injury. This represents a significant health issue because it can cause stretch injuries to the bladder and upper urinary tract complications.

Figure 7C:
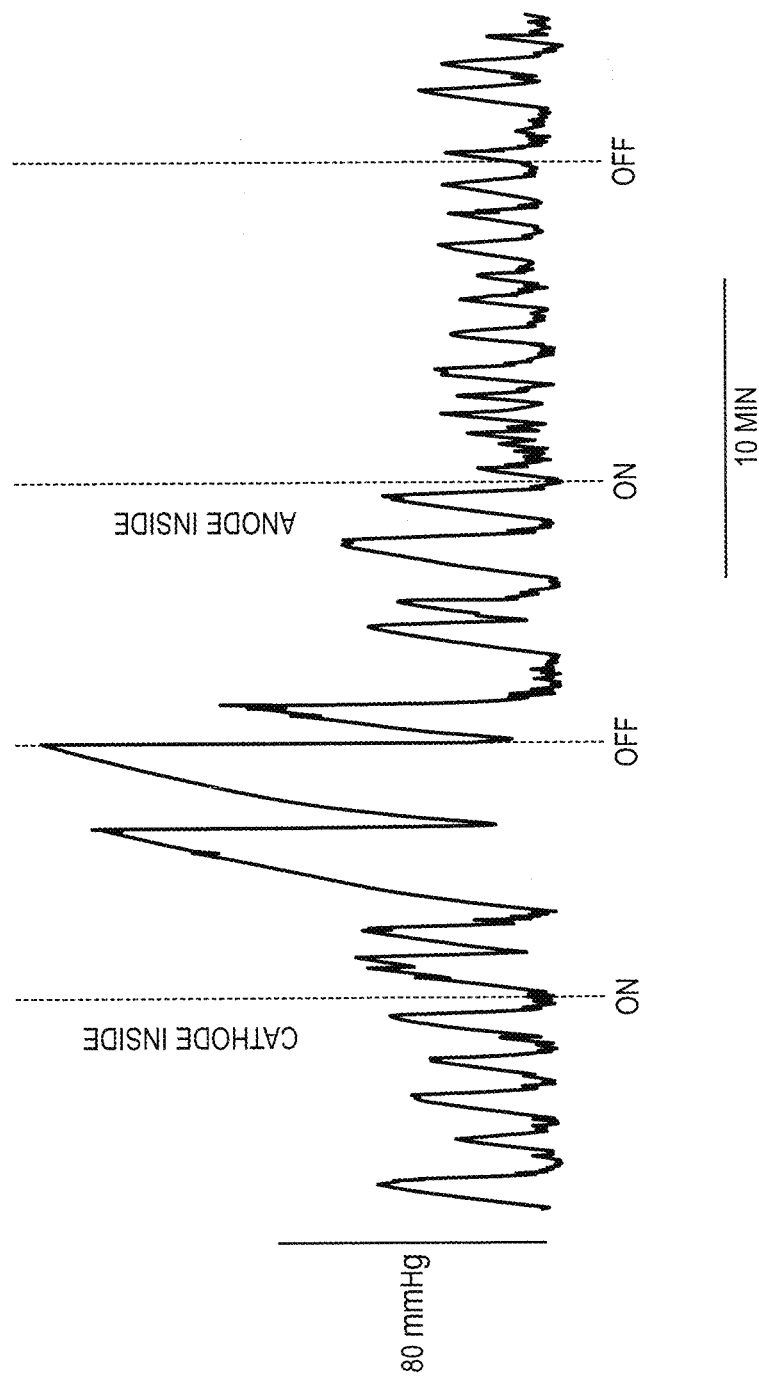
FIG. 7C: shows bladder reflexes in subjects with acute complete spinal cord injury and the effects of tsDCS, in practice of embodiments of the invention.

FIG. 7C shows bladder reflexes in subjects with acute complete spinal cord injury and the effects of tsDCS. Baseline reflexes show very high voiding pressures that were further increased by spinal anode/cathode in bladder arrangement. This effect was maintained for at least 10 min after the current was turned off. When the polarity was switched, with spinal cathode and anode in bladder, this configuration immediately decreased the voiding pressure and decreased inter-voiding contraction interval, demonstrating that this configuration has therapeutically useful effects in subjects with detrusor areflexia following acute spinal cord injury.

These results are consistent with both normal and spinal cord injured mammals. Excitability of small or moderate sized spinal neurons is increased by cathodal tsDCS and depressed by anodal tsDCS. Since autonomic preganglionic neurons are smaller in size, they follow this principle. We have found that cathodal tsDCS on the lumbosacral region increases the excitability of spinal parasympathetic preganglionic neurons hence decreasing urine storage reflexes and increasing voiding reflexes. Reverse polarity induces opposite modulation, i.e., increasing urine storage reflexes and decreasing voiding reflexes. In such practices, we have found that placing the return electrode inside or around the bladder enhances modulatory effects.

The described anodal spinal/cathodal bladder configuration is effective in delaying the bladder voiding reflex to allow for longer filling time. Moreover, the same arrangement produces efficient voiding that is evident in lowering the basal pressure after each voiding cycle. In an illustrative embodiment of the invention, this anodal spinal/cathodal bladder configuration has an inhibitory effect on the parasympathetic input to the bladder. Inhibiting the parasympathetic inputs causes relaxation of the bladder detrusor and contraction of the sphincter vesicae. This allows for longer inter-voiding contraction interval. In addition, this configuration enables increased sympathetic influence over parasympathetic. This treatment is valuable in for achieving conditions of low pressure storage and efficient bladder voiding. In further practices of the invention, we treat conditions of detrusor areflexia by switching the polarities of the electrodes applied to spinal and bladder locations.

Figure 8:
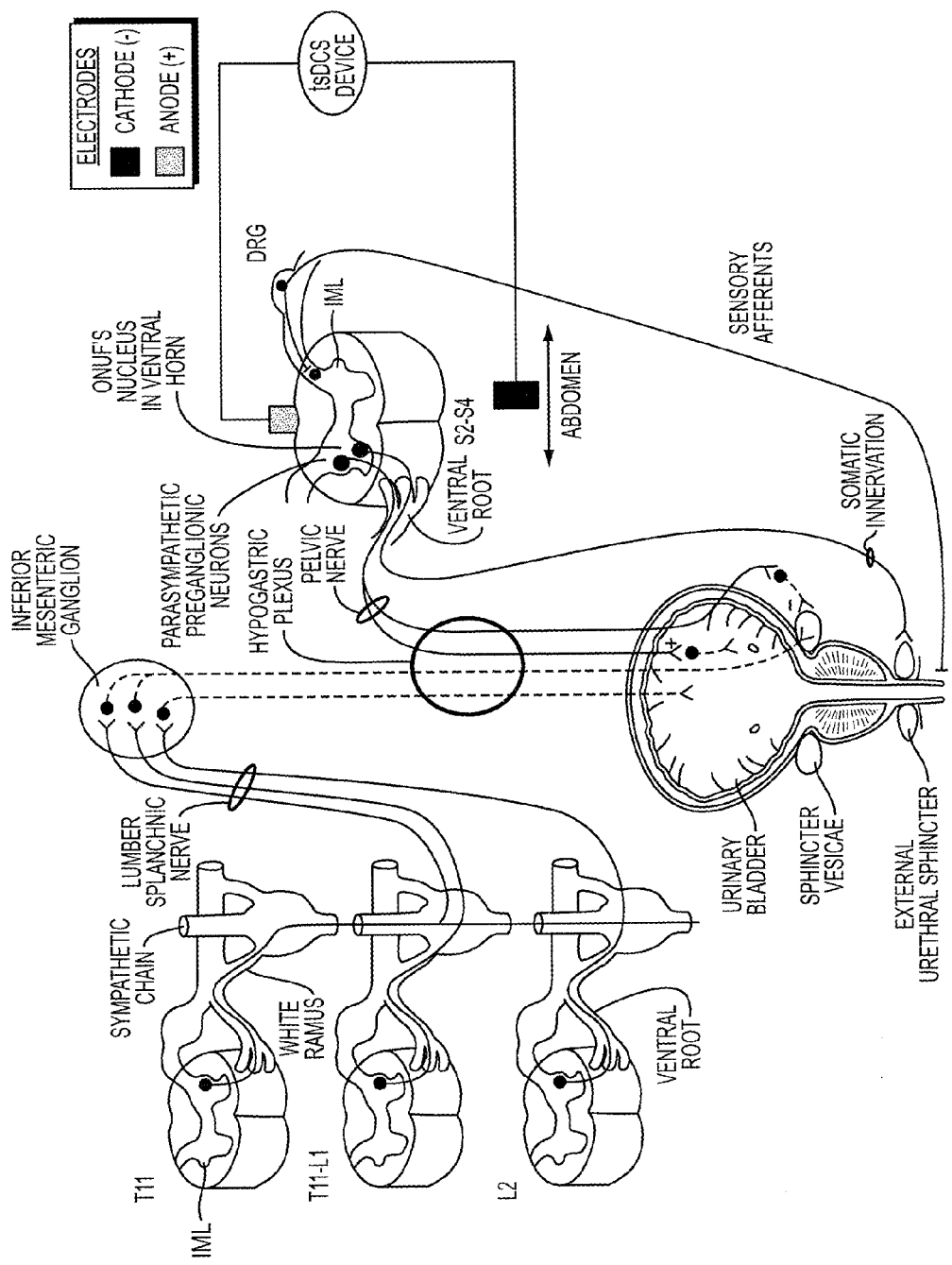
FIG. 8: shows treatment of patient with a condition of urinary incontinence involving detrusor hyperreflexia treated by application of tsDCS in a configuration that decreases parasympathetic tone, in practice of embodiments of the invention.
Figure 9:
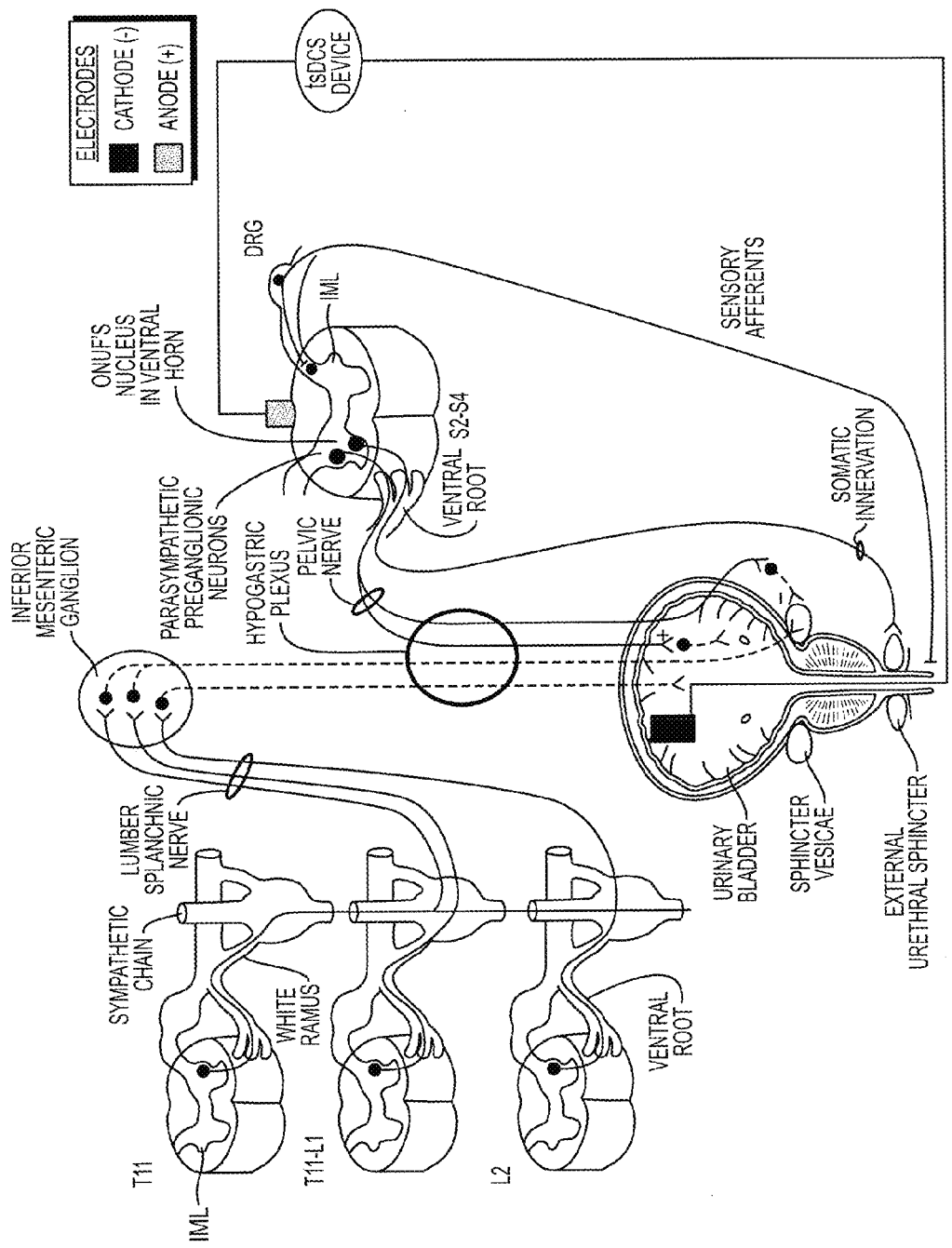
FIG. 9: shows return electrode is positioned within the bladder trans-urethrally, in practice of embodiments of the invention.

In practice of the present invention, a patient with a condition of urinary incontinence involving detrusor hyperreflexia is treated by application of tsDCS in a configuration that decreases parasympathetic tone, FIG. 8. Such a decrease in parasympathetic tone results in relaxation of the detrusor contraction and increased contraction of the sphincter vesicae. In one embodiment this is non-invasively achieved by anodal tsDCS at the level of S2-S4 with a return cathodal electrode positioned anteriorly at an abdominal location, such as the skin superior to the iliac bone. In another embodiment, the return electrode is positioned within the bladder trans-urethrally, FIG. 9. In further practice of the invention these polarities (i.e., the anodal and cathodal assignments,) are reversed for treatment of conditions of urinary retention. In this embodiment, the configuration results in an increase in parasympathetic tone.

Figure 10:
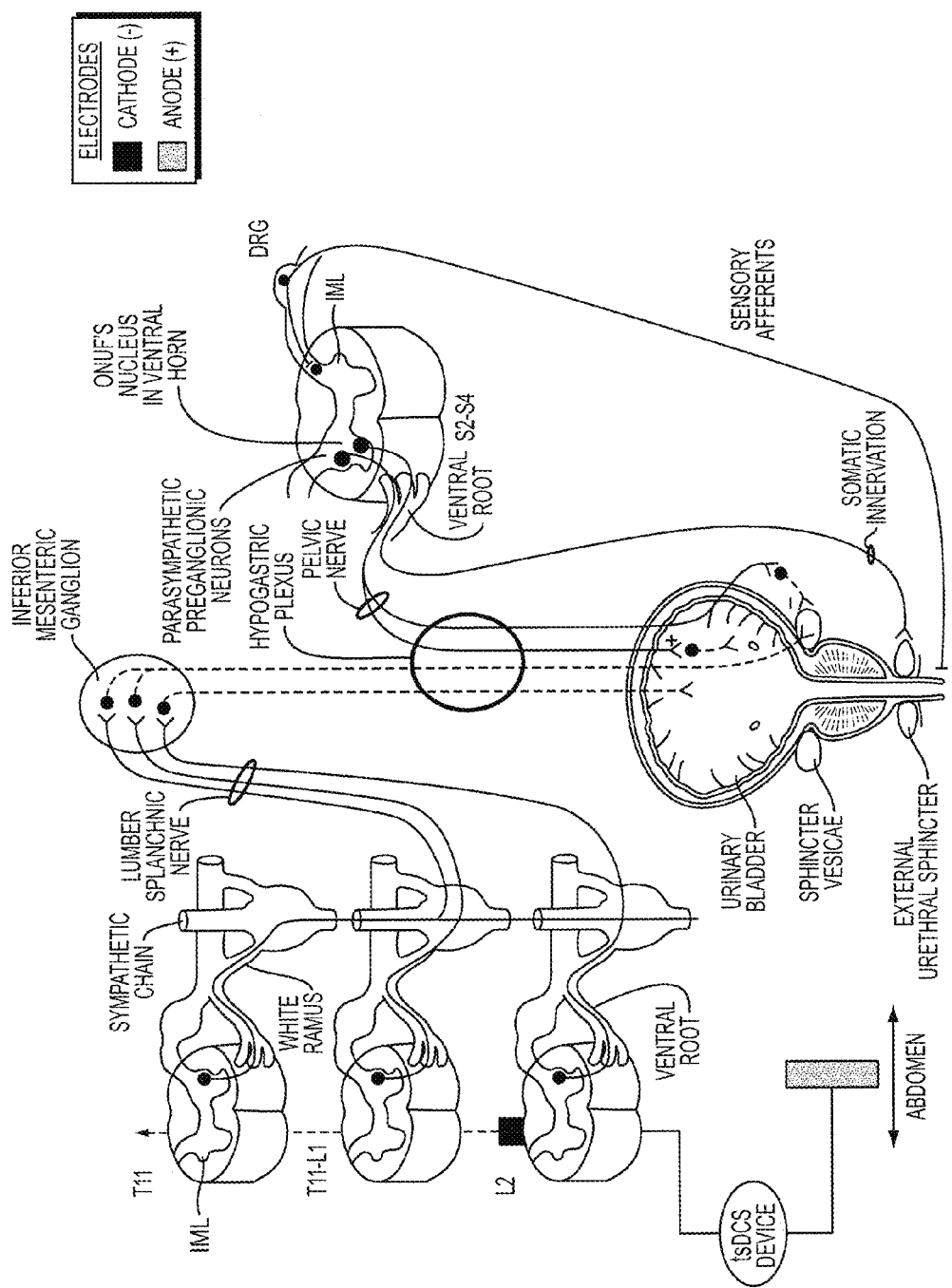
FIGS. 10 and 11: show a subject with a condition of urinary incontinence treated by application of tsDCS in a configuration that increases sympathetic tone with an anodal return electrode abdominally positioned anteriorly (FIG. 10) and at an and with the return electrode positioned within the bladder trans-urethrally (FIG. 11), in practice of embodiments of the invention.
Figure 11:
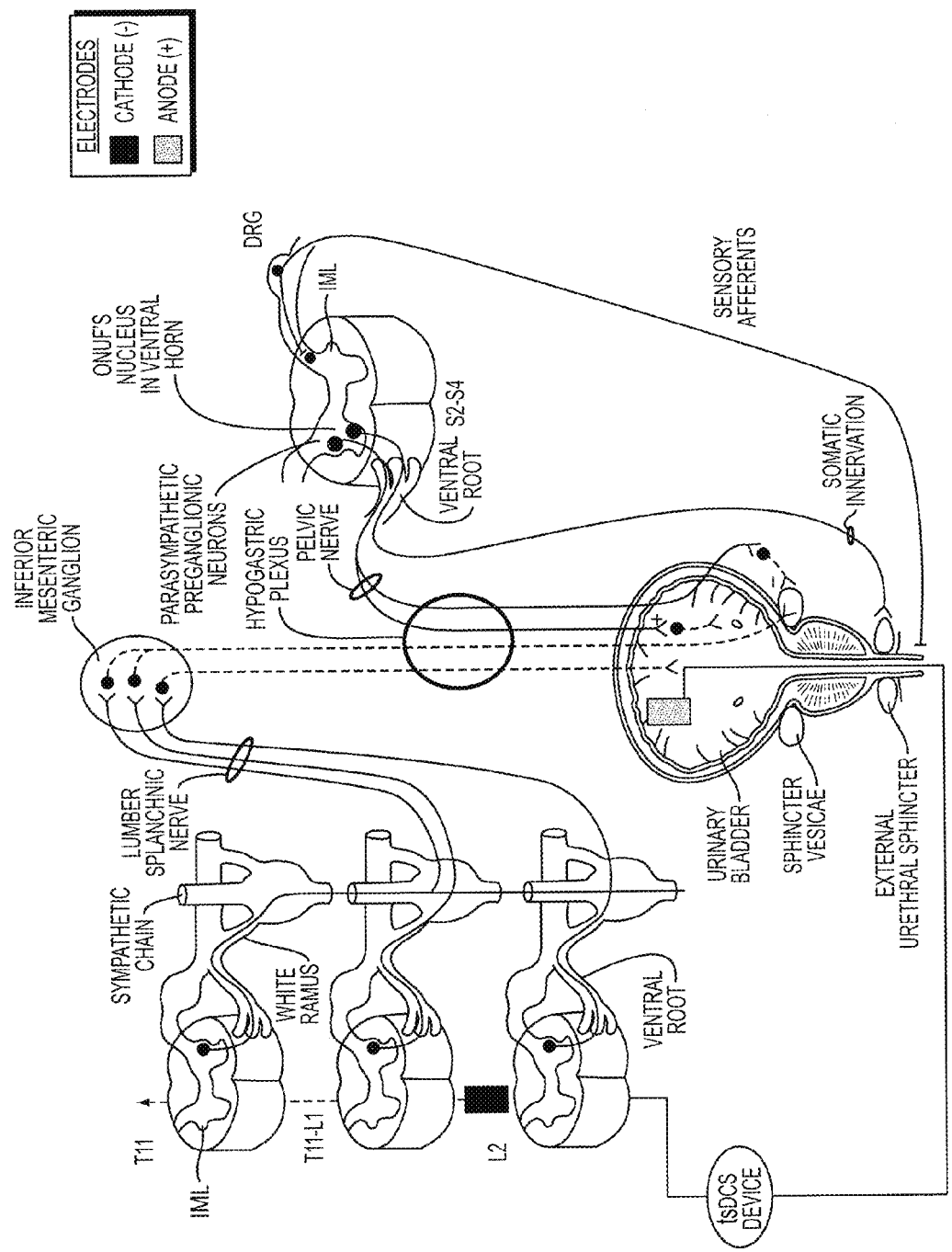

In further embodiments of the present invention, a subject with a condition of urinary incontinence is treated by application of tsDCS in a configuration that increases sympathetic tone, FIG. 10. Such an increase in sympathetic tone results in relaxation and expansion of the detrusor muscle, constriction of the sphincter vesicae, and inhibition of parasympathetic nerves that trigger bladder contraction. This is non-invasively achieved by cathodal tsDCS at the T11-L2 spinal level with an anodal return electrode positioned anteriorly at an abdominal location. In variant of the embodiment, FIG. 11, the return electrode is positioned within the bladder trans-urethrally. In further practice of the invention these polarities (i.e., the anodal and cathodal assignments,) are reversed for treatment of conditions of urinary retention, which achieves a decrease of sympathetic tone.

An embodiment of the invention includes method and system having a single tsDCS stimulation circuit, for mono-stimulation of the spinal cord, and defined by placing an electrode at the spinal location of interest and a return electrode on the anterior aspect of the body, thus defining a pathway of interest between these electrodes. In various practices of the invention, these electrodes are assigned as either anode or cathode and a tsDCS stimulation circuit is thus created for applying current between the electrodes and for modulating spinal cord excitability. The applied current is delivered having a desired signal character and level.

In a wearable mono-stimulation device embodiment of the invention, there are two electrodes which are skin surface type, serving as the active spinal electrode and the return electrode. In one embodiment, the surface of the wearable device provides the spinal electrode and the device also connects to a return electrode on the opposite side of the spinal cord, which is placed on the skin surface such as on the abdomen or iliac crest. In another embodiment, the reference electrode is placed internal to the bladder, such as by urethral catheter insertion, surgically, or the like. The spinal location of interest is selected based on spinal outflow to the target effector organ.

In an implantable mono-stimulation device of the invention, there are two electrodes which are implantable electrodes, serving as the active spinal electrode and the return electrode. In one embodiment, the mono-stimulation device is fully implantable, with electrode leads from the device to dorsal spinal location and ventral location tunneled subcutaneously. The spinal location of interest is selected based on spinal outflow to the target effector organ.

Illustrative Double-Stimulation Embodiments

Beyond strategies that utilize spinal stimulation via tsDCS on its own, we also disclose strategies that combine spinal stimulation via tsDCS with additional stimulation.

We teach double-stimulation in various embodiments. Illustrative embodiments include two stimulators electrically tied together in as system for polarizing a critical neural pathway; a wearable mono-stimulation device communicating wirelessly with an implanted microstimulator; and two separate stimulators that are electrically isolated, as when there is a cortical stimulation using tDCS combined with spinal stimulation using tsDCS. Still other configurations will occur consistent with this disclosure that are also within the scope of the invention.

In one double-stimulation embodiment of the invention, we provide simultaneous tsDCS spinal stimulation together with pulsed peripheral direct current stimulation (pDCS) of a nerve leading to a targeted effector organ. In one particular embodiment, a resulting polarizing circuit is defined between an active spinal tsDCS stimulation circuit and an active pulsed pDCS peripheral stimulation circuit.

Figure 12:
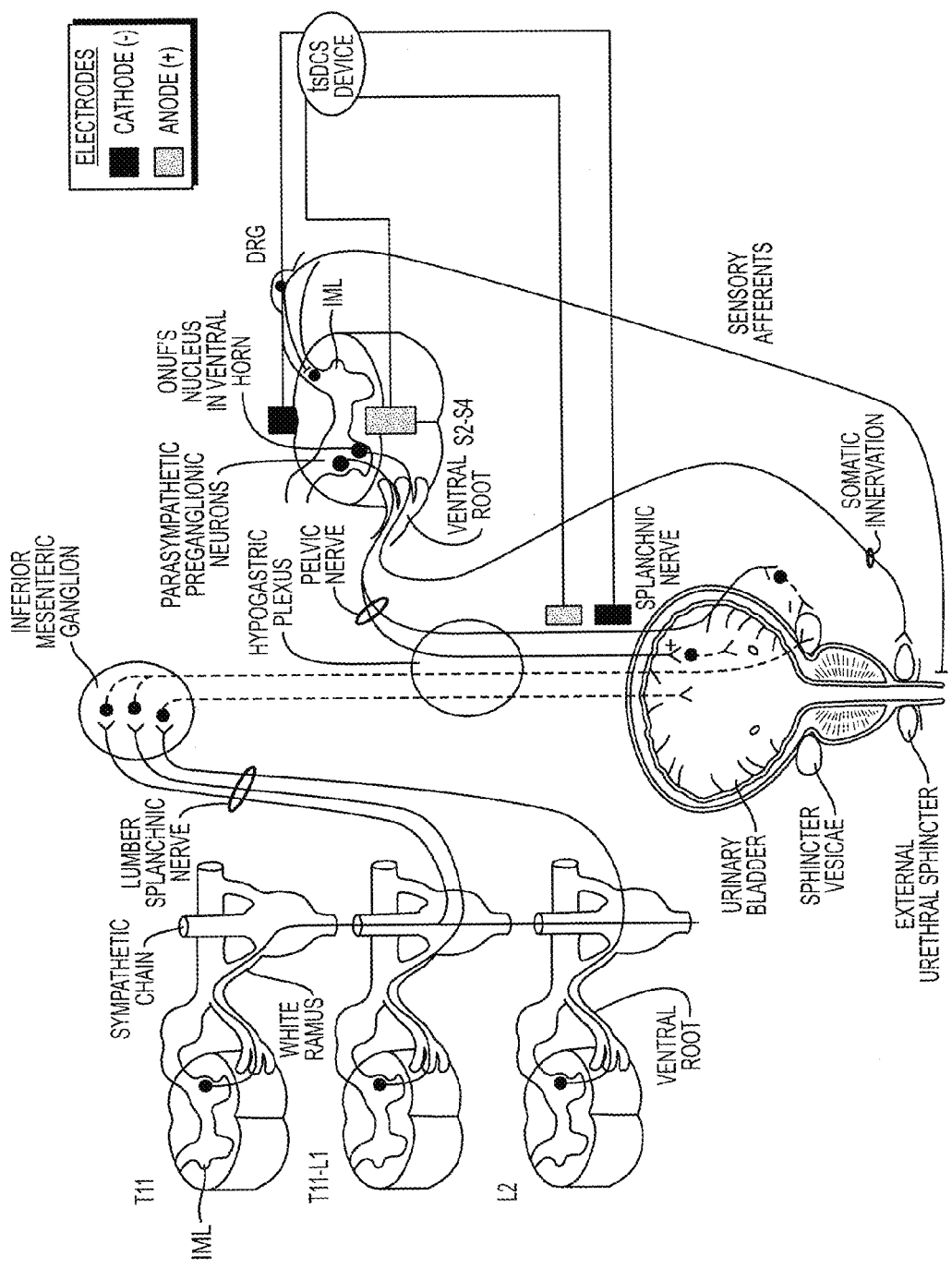
FIG. 12 shows spinal stimulations which increase parasympathetic outflow to the bladder combined with electrical stimulation of the parasympathetic preganglionic fibers in pelvic nerve, with cathodal tsDCS applied at S2-S4, in practice of embodiments of the invention.

In one embodiment of the present invention, the described spinal stimulations which increase parasympathetic outflow to the bladder are combined with electrical stimulation of the parasympathetic preganglionic fibers in pelvic nerve, FIG. 12, with cathodal tsDCS applied at S2-S4. Stimulation of the pelvic splanchnic nerve results in contraction of the bladder detrusor, and relaxation of the sphincter vesicae, thereby further treating a condition of urinary retention. In further practice of the invention, these polarities (i.e., the anodal and cathodal assignments,) are reversed for treatment of conditions of urinary incontinence resulting in a decrease in parasympathetic tone.

Figure 13:
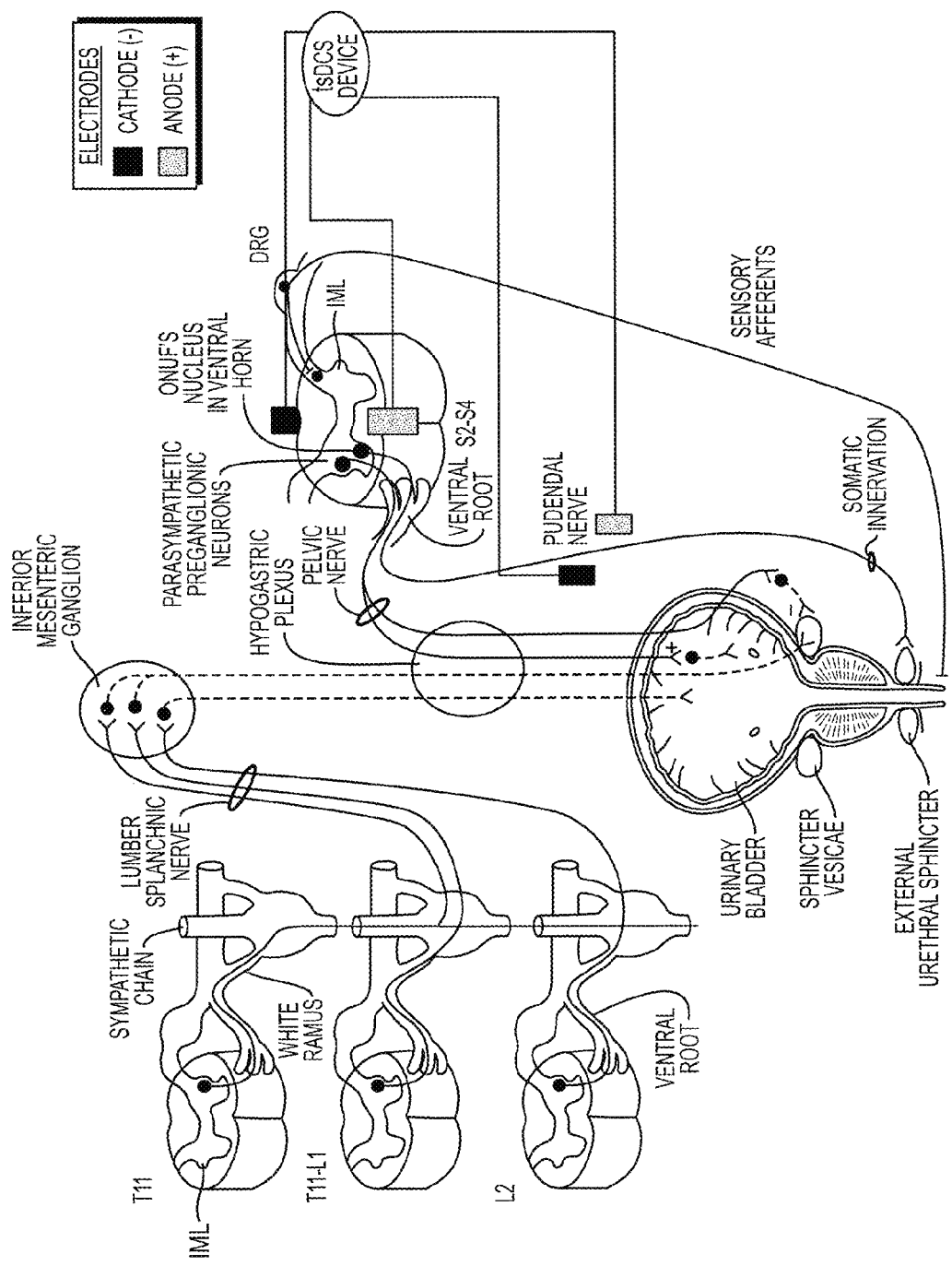
FIG. 13: shows spinal stimulations which increase parasympathetic outflow to the bladder combined with electrical inhibition of the pudendal nerve that innervates the EUS using implanted electrodes, with cathodal tsDCS applied at S2-S4, in practice of embodiments of the invention.

Excessive activity in the somatic efferents innervating the striated muscle of the external urethral sphincter (EUS) results in contraction of the sphincter. In another embodiment of the present invention, the described spinal stimulations which increase parasympathetic outflow to the bladder are combined with electrical inhibition of the pudendal nerve that innervates the EUS using implanted electrodes, FIG. 13, with cathodal tsDCS applied at S2-S4. This combination results in contraction of the bladder detrusor, relaxation of the sphincter vesicae, and relaxation of the EUS, thereby further treating a condition of urinary retention. In further practice of the invention, these polarities (i.e., the anodal and cathodal assignments,) are reversed for treatment of conditions of urinary incontinence and the pudendal nerve innervating the EUS is electrically stimulated using implanted electrodes.

Figure 14:
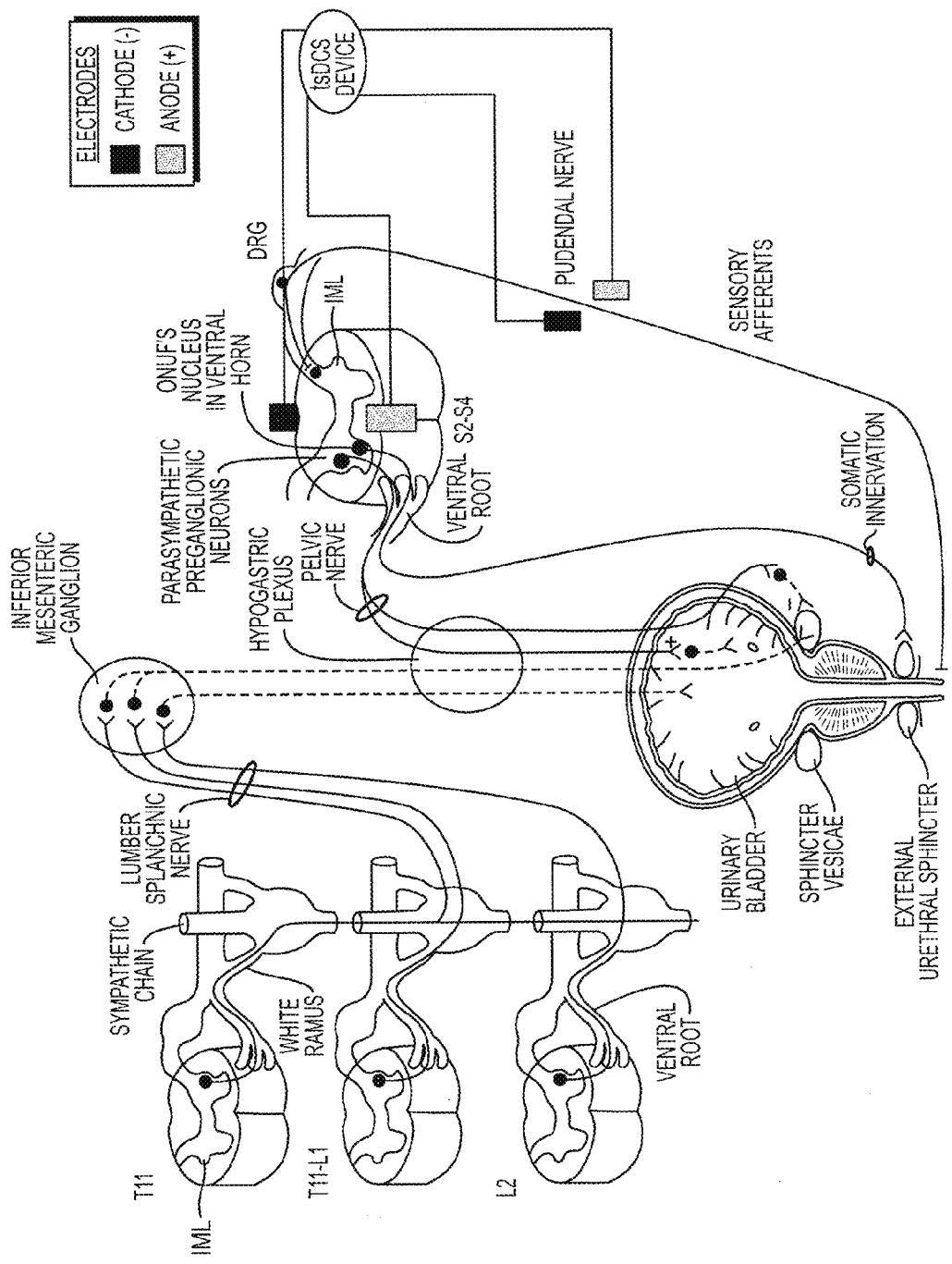
FIG. 14: shows spinal stimulations which increase parasympathetic outflow to the bladder combined with electrical stimulation of the pudendal nerve using implanted electrodes, with cathodal tsDCS applied at S2-S4, in practice of embodiments of the invention.

Stimulation of the sensory afferents that fire in response to urine flow through urethra results in increased strength of bladder contraction and voiding efficiency. In another embodiment of the present invention, the described spinal stimulations which increase parasympathetic outflow to the bladder are combined with electrical stimulation of the pudendal nerve using implanted electrodes, FIG. 14, with cathodal tsDCS applied at S2-S4.

Figure 15:
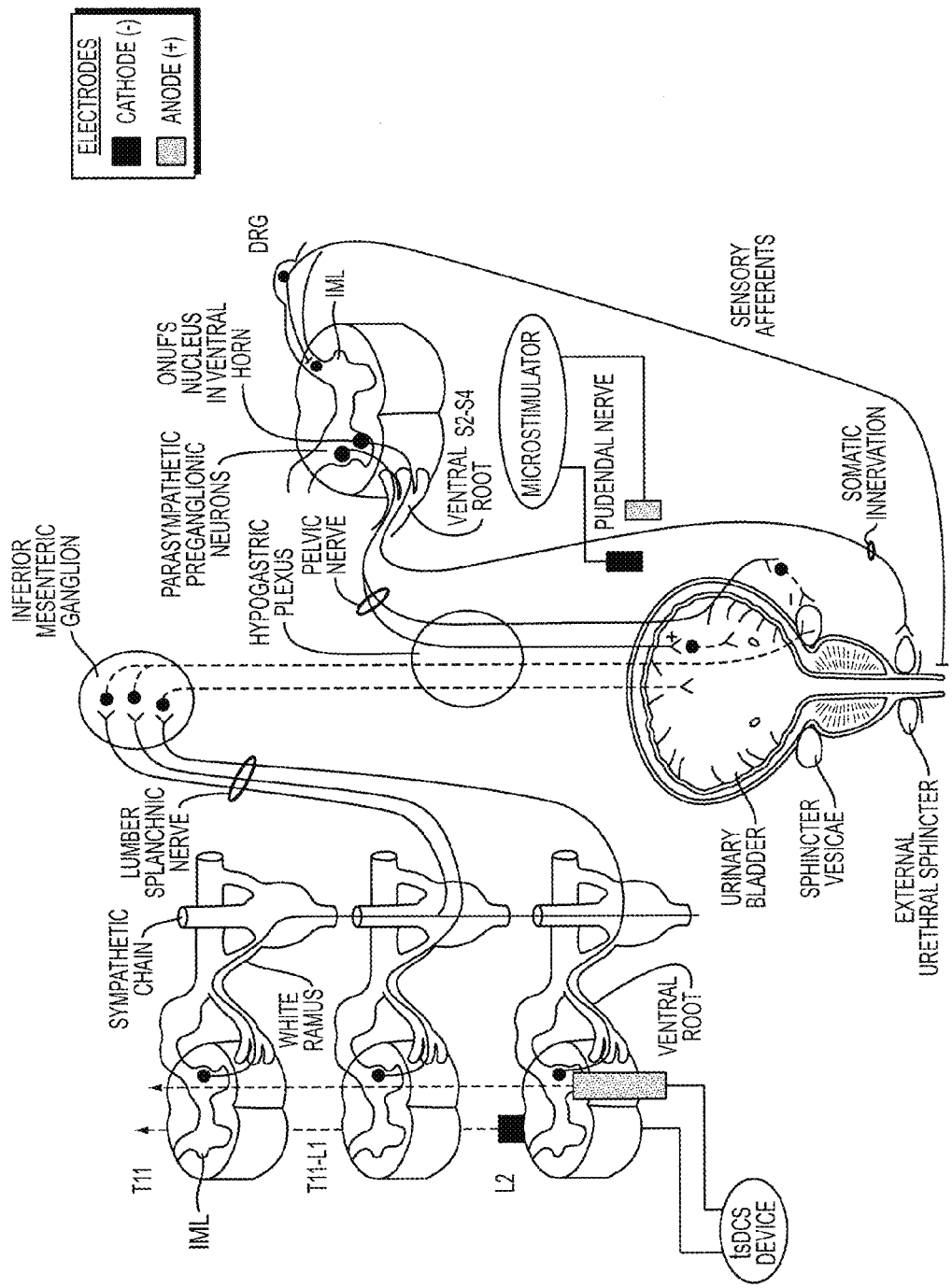
FIG. 15: shows cathodal spinal stimulations increase sympathetic outflow to the bladder combined with implanted microstimulator electrodes which stimulate the pudendal nerve, with cathodal spinal stimulations at T11-L2, in practice of embodiments of the invention.

In a further embodiment, cathodal spinal stimulations increase sympathetic outflow to the bladder as combined with implanted microstimulator electrodes which stimulate the pudendal nerve, FIG. 15, with cathodal spinal stimulations at T11-L2. Increased sympathetic tone results in relaxation of the bladder detrusor and contraction of the sphincter vesicae, while stimulation of the pudendal nerve results in contraction of the external urethral sphincter, thereby further treating a condition of urinary incontinence. In further practice of the invention, these polarities (i.e., the anodal and cathodal assignments,) are reversed for treatment of conditions of urinary retention and the pudendal nerve innervating the EUS is electrically inhibited using implanted electrodes. In such embodiments, the implanted microstimulator communicates with and is controlled by a tsDCS controller that provides spinal stimulations, that can be either a wearable device, or an implanted subcutaneous device.

Figure 16:
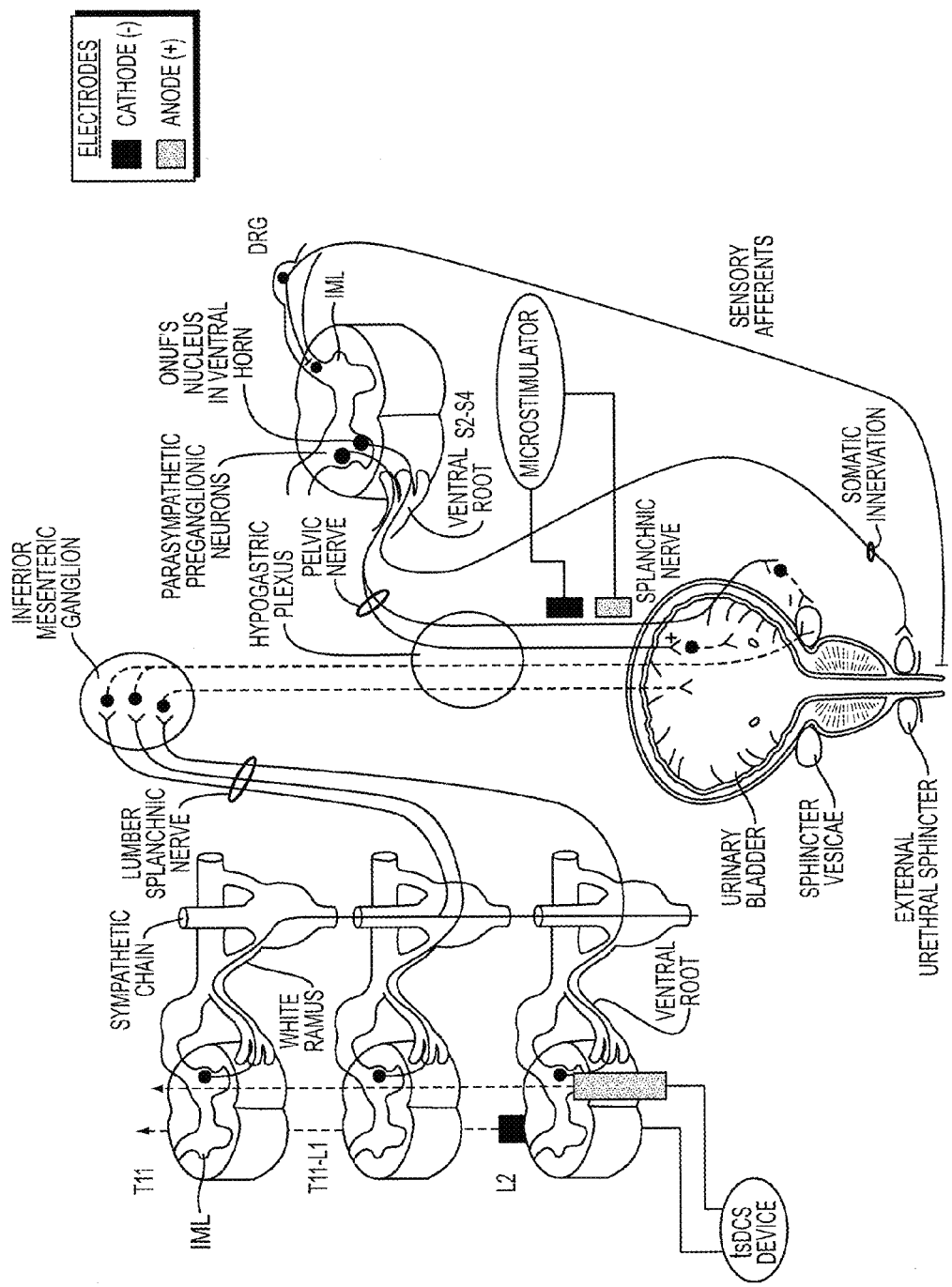
FIG. 16: shows cathodal spinal stimulations which increase sympathetic outflow to the bladder combined with implanted electrodes which are applied to inhibit the parasympathetic preganglionic fibers of the pelvic splanchnic nerves, with cathodal spinal stimulations at T11-L2, in practice of embodiments of the invention.

In a further embodiment, the cathodal spinal stimulations which increase sympathetic outflow to the bladder are combined with implanted electrodes which are applied to inhibit the parasympathetic preganglionic fibers of the pelvic splanchnic nerves, FIG. 16, with cathodal spinal stimulations at T11-L2. Increased sympathetic tone results in relaxation of the bladder detrusor and contraction of the sphincter vesicae, while inhibition of the pelvic splanchnic nerves results in further relaxation of the bladder detrusor, thereby further treating a condition of urinary incontinence. In further practice of the invention, these polarities (i.e., the anodal and cathodal assignments,) are reversed for treatment of conditions of urinary retention.

In a fully implantable subcutaneous double-stimulation embodiment of the invention, two circuits are supplied by four leads emanating from controller device. This embodiment delivers two simultaneous stimulations, a spinal stimulation and a peripheral stimulation applied to a nerve of the target effector organ. There are two separate stimulation current paths with these two circuits. But these circuits also interact to form a resulting stimulation current path between the anode of one circuit (i.e., active electrode at the spine of the spinal circuit) and the active cathode at the nerve of the neural circuit. This provides a polarization flow down along the neural path between the two active electrodes. In this double stimulation embodiment, the first current path is a tsDCS spinal circuit defined by placing an active spinal electrode at the spinal location of interest and a return electrode at a non-spinal location, with the applied current running across the tissues between these electrodes. The second current path is a peripheral circuit defined by placing active cathode and anode electrodes on or in proximity to a nerve of the target effector organ.

In a further embodiment, a two-part semi-implantable stimulation device is provided. A first component is a wearable mono-stimulation device which includes an active spinal electrode applied by skin attachment and a return electrode. The second component is an implanted peripheral stimulator or microstimulator with two leads that has its own power supply. Both leads of the second component are in contact with or in close proximity to a nerve of a target effector organ. The wearable component can communicate wirelessly with the implanted component. When the wearable component turns on and issues its stimulation signal, the implanted stimulator responds and issues a stimulation signal to the target effector organ, which can be either excitatory or inhibitory.

In a further embodiment of a wearable double-stimulation device, two circuits are supplied by four leads emanating from controller device. This embodiment delivers two simultaneous stimulations. The first stimulation is a spinal stimulation delivered via active spinal electrode applied by skin attachment and a return electrode. The second stimulation modulates central autonomic outflow, and can be either trans-cranial direct current stimulation (tDCS) or trans-cutaneous vagal nerve stimulation (tVNS). There are two separate stimulation current paths with these two circuits that are electrically isolated from each other.

Triple-Stimulation Embodiments

Figure 17:
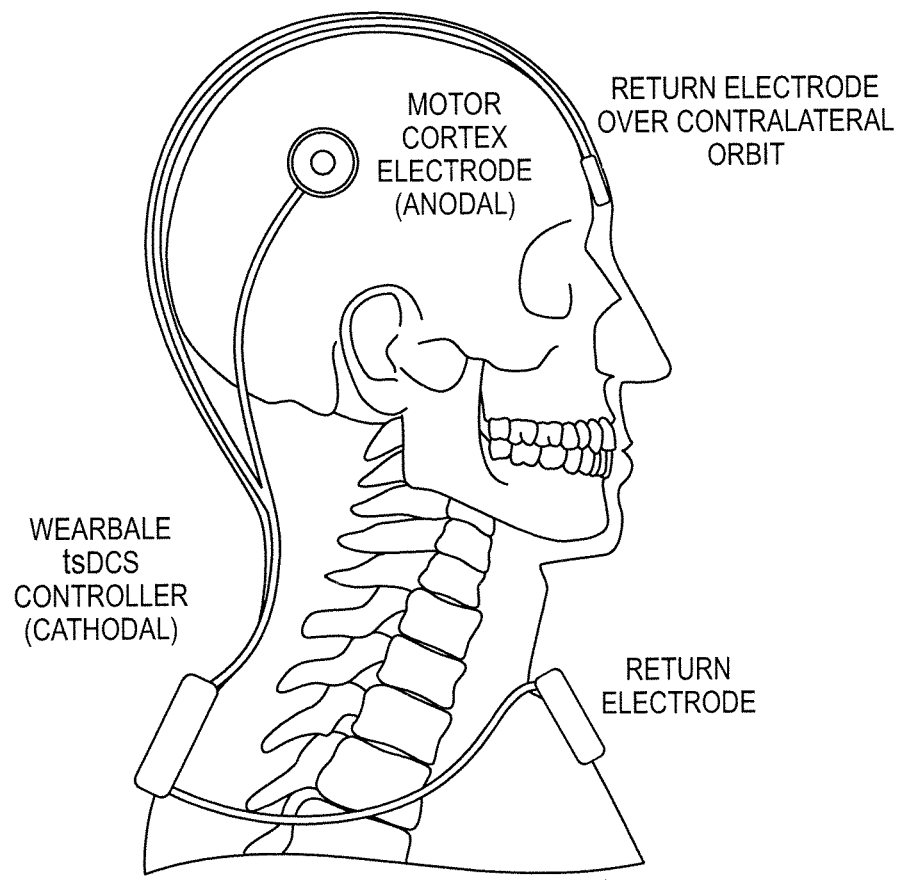
FIG. 17: shows non-invasive tDCS coupled with tsDCS at the relevant spinal level to modulate autonomic outflow, with sympathetic outflow from the brain increased by anodal tDCS over the primary motor cortex and further increased at the spinal level of the targeted effector organ by cathodal tsDCS at the high thoracic level, in practice of embodiments of the invention.

We also herein describe strategies that combine spinal stimulation, peripheral stimulation, and stimulation of central autonomic outflow to modulate autonomic function. The previously disclosed strategies based on mono-stimulation and double-stimulation might be sufficient for certain applications. In other applications, it will be necessary or beneficial to directly modulate central autonomic outflow before spinal level modulation via tsDCS and potential peripheral stimulation. Non-invasive methods for modulating central autonomic outflow are combined with other sites of stimulation using a variety of approaches:

Transcranial direct current stimulation (tDCS)—A number of different tDCS montages have been utilized to modulate the autonomic nervous system. Anodal tDCS over the primary motor cortex, with cathode return electrode over the contralateral supraorbital area has been reported to increase sympathetic activity (Clancy et al., Brain Stim., 2014, 7:97-104). Anodal stimulation of the left dorsolateral prefrontal cortex (DLPFC) has been reported to increase parasympathetic activity, while anodal stimulation of the right DLPFC has been reported to increase sympathetic activity (Brunoni et al., Psychoneuroendocrinology, 2012). Other work has reported that anodal tDCS over the temporal lobe results in increased parasympathetic activity. As such, non-invasive tDCS can be coupled with tsDCS at the relevant spinal level to modulate autonomic outflow. In one embodiment, sympathetic outflow from the brain is increased by anodal tDCS over the primary motor cortex and further increased at the spinal level of the targeted effector organ by cathodal tsDCS at the high thoracic level. This embodiment is shown in FIG. 17, where cortical electrodes are shown combined with a wearable tsDCS controller. In another embodiment, sympathetic outflow from the brain is increased by anodal tDCS of the right DLPFC and further increased at the spinal level of the targeted effector organ by cathodal tsDCS. In yet another embodiment, parasympathetic outflow from the brain is increased by anodal tDCS over the temporal lobe and further increased at either the S2-S4 spinal level of the targeted effector organ or the brainstem level of DMV by cathodal tsDCS.

Figure 18B:
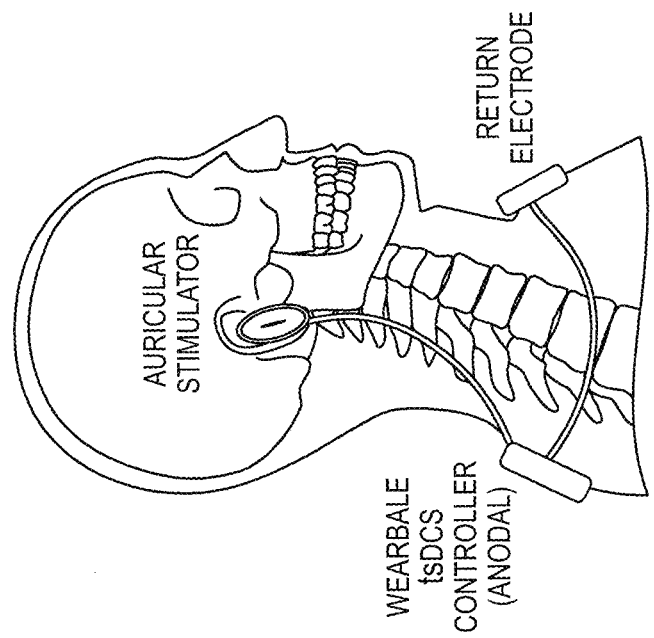
FIG. 18A-B: shows transcutaneous vagal nerve stimulation (tVNS) and an embodiment where auricular stimulation is combined with a wearable tsDCS controller, in practice of embodiments of the invention.
Figure 18A:
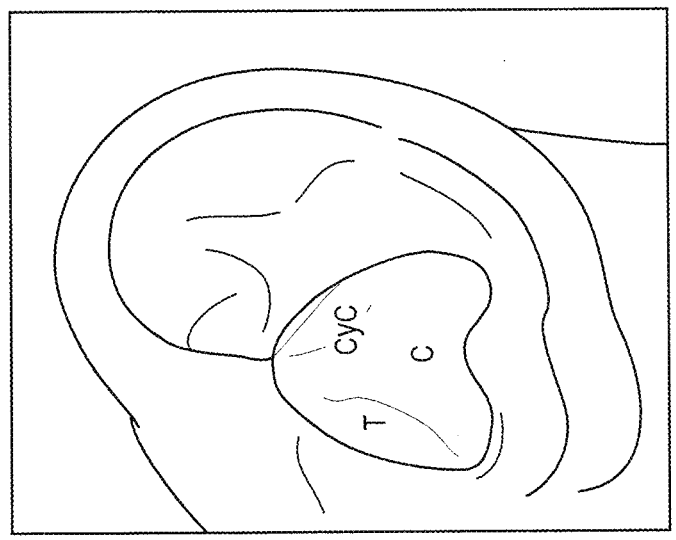

Transcutaneous vagal nerve stimulation (tVNS)—The auricular branch of the vagus nerve supplies sensation to the posterior parts of the ear pinna, external auditory canal and tympanic membrane, FIG. 18A. Nerve cell bodies are located in the superior (jugular) ganglion of the vagus, and they project to the nucleus of the tractus solitarius (NTS) in the brainstem. Electrical stimulation of the ear concha (tVNS) produces activation of NTS and its known projections (parabrachial nucleus, nucleus accumbens, hypothalamus, amygdala). The dorsal motor nucleus of the vagus (DMV) in the brainstem contains the cell bodies of the parasympathetic neurons that project down the vagus nerve as preganglionic efferent fibers. Direct connections between the NTS and DMV have been described, and it is established that NTS sends projections to DMV. Stimulation of the external ear tragus using electrical stimulation (10-50 mA, 30 Hz pulse frequency, 200 microsecond pulse width) results in decreased sympathetic discharge (Clancy et al., Brain Stim., 2014, 7:817-877. In a practice of the present invention, we utilize this non-invasive methodology for decreasing sympathetic tone and coupling it with anodal tsDCS at the spinal level. Sympathetic outflow from the brain is reduced by tVNS and further reduced at the spinal level of the targeted effector organ by applied anodal tsDCS. This embodiment is shown in FIG. 18B, where auricular stimulation is combined with a wearable tsDCS controller.

Transcranial magnetic stimulation (TMS)—TMS, both repetitive and single pulse, has been utilized in studies that modulate the autonomic nervous system. Targeted sites include left temporo-parietal cortex (Lai et al., 2010) and primary motor cortex M1 (Vernieri et al., 2009 and Yozbatiran et al., 2009). TMS was found to exert changes on autonomic control in these, and other studies. Accordingly, in a further embodiment we combine TMS with tsDCS at the spinal level. While FIG. 17 is illustrated showing cortical stimulation via tDCS, it will be appreciated that TMS is an alternative source of cortical stimulation in practices of the present invention.

Cold/hot pressors—It is known that immersion of a subject's hand in a bucket of ice water results in increased heart rate and pulse pressure, thought to be due to increased sympathetic tone activated by sensory afferents. As such, in practices of the invention, we utilize this approach as a methodology to initiate modulation of autonomic outflow. As a bucket of ice water is impractical, we utilize alternative methodologies to achieve this effect. More specifically, in one embodiment, this effect is delivered as a cooling/heating pad that is affixed to a thermosensitive area of skin such as the upper back, or in another embodiment is presented as a vest or glove with cooling/heating elements. This device is switched to either "cold stimulation" or "hot stimulation" to provide that sensation to the skin. To increase sympathetic tone to a specific effector organ, we combine activation of "cold stimulation" to the subject's skin with cathodal tsDCS at the relevant spinal level. To increase parasympathetic tone to a specific effector organ, we combine activation of "hot stimulation" to the subject's skin with cathodal tsDCS at the S2-S4 level (or DMV brainstem level). In this way, efferent outflow through either the sympathetic or parasympathetic system is activated depending on which temperature "setting" is used, and cathodal tsDCS amplifies the signals that are going to autonomic neurons in the spinal cord.

Figure 19:
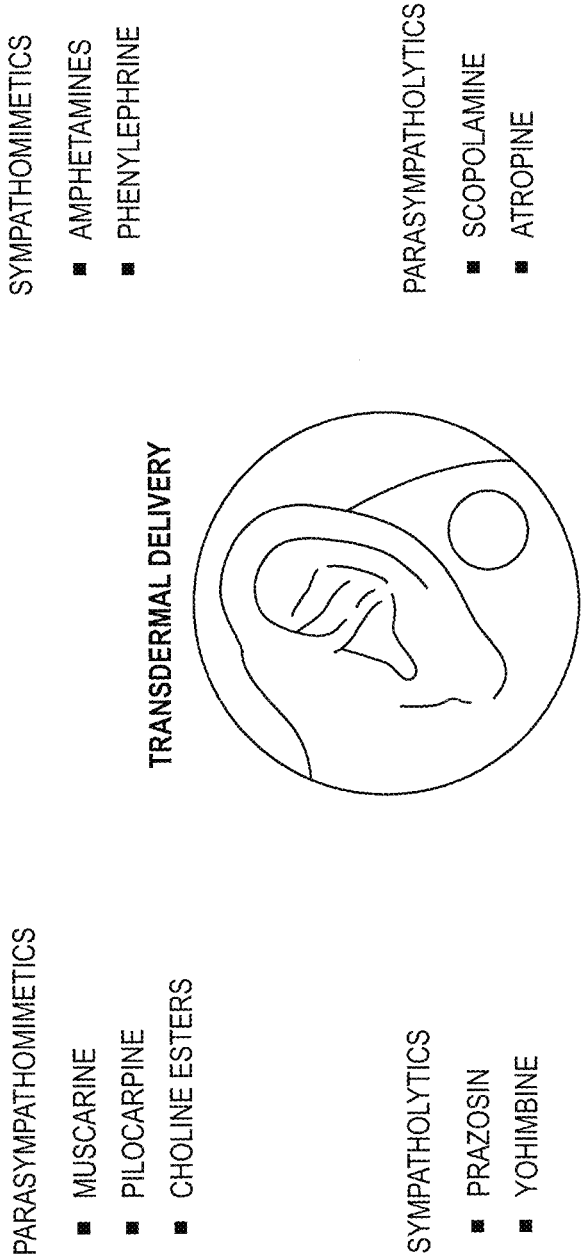
FIG. 19: shows pharmacological autonomic modulators, in practice of embodiments of the invention.

Pharmacological autonomic modulators—Certain pharmacological agents have modulatory effects on the autonomic nervous system. Sympathomimetics increase sympathetic tone, and include amphetamines and phenylephrine. Sympatholytics decrease sympathetic tone, and include prazosin and yohimbine. Parasympathomimetics increase parasympathetic tone, and include muscarine, pilocarpine and choline esters. Parasympatholytics decrease sympathetic tone, and include scopalamine and atropine. Sympathomimetics can be given in combination with parasympatholytics, and parasympathomimetics can be given in combination with sympatholytics. Depending on specific molecular characteristics, these pharmacological agents can be given orally, subcutaneously, intramuscularly, transdermally, intravenously or as depot injections. Pharmacological autonomic modulators are shown in FIG. 19.

As will be understood by a person skilled in the art, in practices of the present invention, we modulate autonomic outflow and use various strategies to monitor effect. For example, in various embodiments, we monitor readouts including heart rate, heart rate variability, microneurography recording muscle sympathetic nerve activity, blood pressure, pulse pressure, pupillary size, skin conductance, sympathetic skin response, respiratory rate, cerebral vasomotor reactivity, and body temperature, the utility of which will be understood by a person skilled in the art.

Figure 20:
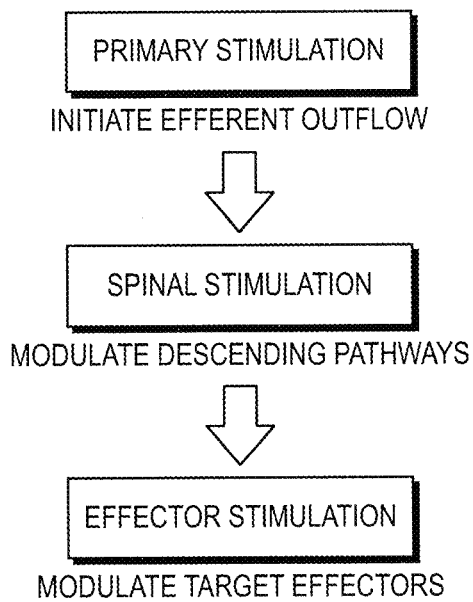
FIG. 20: shows a triple-stimulation approach in practice of embodiments of these teachings, in practice of embodiments of the invention.

In another embodiment, various of the above described approaches of modulating central autonomic outflow, is combined with spinal stimulation and is further combined with a third peripheral stimulation, delivered at the level of the nerve leading to the target effector organ, to render a useful therapeutic effect. This triple-stimulation approach is shown in FIG. 20.

In a further embodiment, a two-part semi-implantable stimulation device is provided. A first component is a wearable double-stimulation device that provides a first stimulation that is spinal stimulation, and a second stimulation that modulates central autonomic outflow. The second component is an implanted peripheral stimulator or microstimulator with two leads that has its own power supply. Both leads of the second component are in contact with or in close proximity to a nerve of a target effector organ. The wearable component can communicate wirelessly with the implanted component. When the wearable component turns on and issues its stimulation signal, the implanted stimulator responds and issues a stimulation signal to the target effector organ, which can be either excitatory or inhibitory.

In various embodiments, effector organ stimulation via the nerve leading to the effector organ is achieved using energetic modalities, including electrical stimulation, magnetic stimulation, acoustic stimulation and others. In some instances, it is desirable to directly stimulate such nerve using electrical stimulation. In several embodiments of the invention, the electrical stimulation is applied at the nerve leading to smooth muscle, skeletal muscle or is at a ganglion or plexus associated with the targeted effector organ. In some embodiments applied to the autonomic system, stimulation is applied directly at the sympathetic trunk or ganglia, celiac ganglion, superior mesenteric ganglion, inferior mesenteric ganglion, or is stimulated at the post-ganglionic nerve. The parasympathetic nervous system has ganglia in close proximity to or located in the organs being innervated, and in some embodiments electrodes are placed in proximity to these parasympathetic ganglia to achieve the desired simulative effect at the target effector organ.

Peripheral pulse intensity typically ranges is from 5 to 40 mA. In one triple stimulation bladder embodiment, continuous tsDCS is applied to the Onuf's nucleus in the sacral region of the spinal cord. The tsDCS is applied with typical intensity in the range from 2 to 5 mA.

Peripheral pulse intensity typically ranges is from 5 to 40 mA. In one triple stimulation bladder embodiment, continuous tsDCS is applied to the Onuf's nucleus in the sacral region of the spinal cord. The tsDCS is applied with typical intensity in the range from 2 to 5 mA.

In treating bladder dysfunction, the desired subthreshold spinal tsDCS and subthreshold pDCS are established in view of the level at which the effector organ responds to electrical stimulation, which serves as the threshold indicator and value of merit. In an embodiment, this level is in a range of 2-5 mA. In an illustrative embodiment, 3-4.5 mA stimulation at the spine and 2-3 mA via the cathetered active peripheral electrode or 2.5-3.5 mA when applied via abdominal surface electrode, delivers the desired subthreshold peripheral stimulation, assuming the return electrode is placed at a bony location. If the peripheral return electrode is located closely associated with the bladder, such as by placement near the bladder or into the bladder, then the threshold is detected and adjusted accordingly, typically in the same range.

The embodiments described herein provide the basis to treat neurogenic bladder conditions that result in either detrusor hyperreflexia or detrusor areflexia with external devices, wearable devices, or implanted devices that deliver the described stimulations. It will be appreciated by a person skilled in the art that the findings described herein and reduced to practice for bladder modulation using a tsDCS-based approach are directly applicable to controlling kidney, lung, heart, pancreas, gastrointestinal system, stomach, anal sphincter and other autonomically controlled effector organs and may be practiced accordingly under the principals disclosed herein. It will now be appreciated that we have illustrated single, double, and triple stimulation configurations and methods in practice of embodiments of the invention.

Some of the above described approaches combine a primary stimulation that modulates either the sympathetic or parasympathetic branch of the autonomic nervous system, with spinal stimulation that amplifies the evoked response. A single constant tsDCS stimulation impacting the target effector organ is useful and successful in certain situations. In other situations, a double-stimulation approach is useful in situations where amplifying autonomic outflow at the spinal level is sufficient for a therapeutic effect. In other situations, primary stimulation and spinal stimulation is combined with a third stimulation, which is delivered at the level of the nerve leading to the targeted effector organ, to render a useful therapeutic effect. Effector organ stimulation via the nerve leading to the effector organ is achieved using selected energetic modalities, including electrical stimulation, magnetic stimulation, acoustic stimulation and others. In some instances, it is desirable to directly stimulate a nerve using electrical stimulation. The electrical stimulation is directed to the nerve leading to smooth muscle, skeletal muscle or is at a ganglion or plexus associated with the ANS. This is directly at the sympathetic trunk or ganglia, celiac ganglion, superior mesenteric ganglion, inferior mesenteric ganglion, or is stimulated at the post-ganglionic nerve. The parasympathetic nervous system has ganglia in close proximity to or located in the organs being innervated, and in some instances electrodes might be placed in proximity to these parasympathetic ganglia.

In another embodiment, stimulation of the motor cortex using TMS or tDCS is combined with spinal stimulation using tsDCS and peripheral stimulation of a nerve leading to a striated muscle under voluntary control. As it relates to bladder dysfunction, this approach can be utilized to strengthen the external urinary sphincter (EUS), which is a striated muscle under voluntary control. In a preferred embodiment, TMS is applied to the motor cortex area associated with the EUS, cathodal tsDCS is applied at the spinal level corresponding to EUS, and peripheral stimulation is applied to the pudendal nerve leading to the EUS using an implanted electrode. In one practice of this embodiment, wherein neural dysfunction of a distal effector organ (e.g., a urinary sphincter) is to be treated, the tsDCS spinal stimulation is applied for the duration of treatment (a "session") to the spine at the spinal location and affecting a neural pathway associated with neural control of that effector organ, and peripheral and cortical stimulations are applied to locations associated with that effector organ to improve neural communication to that target effector organ. In another embodiment, this approach is applied to the external anal sphincter.

In an illustrative triple stimulation embodiment of the invention, pulsed stimulation and cortical stimulation are applied in the presence of tsDCS at the spinal location (neural spinal junction) of interest (i.e., a neural spinal junction associated with cortical control of a target peripheral organ of interest, such as the bladder). The cortical, spinal and peripheral stimulation sites are connected by a common neural pathway. As applied to the neural pathway, applied peripheral stimulation pulses from a peripheral stimulator device (e.g., device 14) are synchronized with applied cortical stimulation pulses from a cortical stimulator 12 or 12A, such that the peripheral pulses precede the cortical pulse in timing, in any one cycle. In a typical stimulation cycle, at least one peripheral pulse and preferably two, applied to the peripheral location of interest, e.g., a nerve associated with bladder sphincter control, precede a following cortical pulse, wherein such cortical electrical or magnetic stimulation pulse is applied at a cortical location of interest, such as at a cortical site associated with control of the target organ, e.g., control of bladder sphincter. Latencies of induced peripheral and cortical pulses are synchronized to give maximal evoked response (MEP), wherein latencies typically range from 20 to 45 ms, and as will be appreciated by a person skilled in the art, the timing of the applied pulses is thus adjusted in view of these latencies in order to induce the cortical and pulsed neural signals on the neural pathway of interest as will flow to the spinal junction and overlap at the spinal junction together in the applied presence of the tsDCS stimulation, to achieve the desired triple stimulation. Peripheral pulse intensity typically ranges from 5 to 40 mA. In one triple stimulation bladder embodiment, the tsDCS is applied to the Onuf's nucleus in the sacral region of the spinal cord. tsDCS with typical intensity in the range from 2 to 5 mA.

It will be appreciated that in practice of an embodiment of the invention, we limit maximum current output for double-stimulation with two simultaneous skin-surface DC stimulations at or about 5 mA for both spinal and peripheral stimulation locations. In one embodiment, an illustrative sponge rubber electrode has a skin contact area of 9 cm2 resulting in a maximum current density of 0.56 mA/cm2. As will be appreciated by a persons skilled in the art, this is well below the reported safe upper limit for current density of 14.29 ma/cm2 as cited in: Nitsche M A, Liebetanz D, Lang N, Tergau F, Paulus W., in Safety Criteria For Transcranial Direct Current Stimulation (TDCS) In Humans. Clin Neurophysiol 2003; 114(11):2220e2."

It will be appreciated that the stimulation routines of the invention utilizing cortical stimulation, either direct electrical direct current stimulation or magnetic, as in TMS, follow the triple stimulation teachings of our co-pending U.S. application Ser. No. 14/665,220, filed Mar. 23, 2015, entitled: Method and System for Treatment of Neuromotor Dysfunction, which is a continuation of now issued U.S. Pat. No. 9,011,310, all having a common inventor and assigned to a common owner, and all incorporated herein by reference for all purposes whatsoever.

It will be appreciated that the stimulation teachings of the invention utilizing double stimulation are an adaptation of the teachings of our co-pending U.S. application Ser. No. 15/046,797, filed Feb. 18, 2016, entitled: Trans-Spinal Direct Current Modulation Systems, which is a continuation of now issued U.S. Pat. No. 9,283,391, all having a common inventor and assigned to a common owner, and all incorporated herein by reference for all purposes whatsoever. In a further alternative illustrative embodiment of the invention, pulsed implanted stimulation is provided, as is known in the art for other pulsed peripheral applications. Such stimulation can be set to an output of up to 10.5V for pulses up 240 microseconds at 14 Hz, 0.3% duty cycle, providing a set voltage amplitude and adjusting the current to maintain the set amplitude, with pulsed current up to 10 mA. Voltage settings are set according to what the patient can tolerate, as will be appreciated by a person skilled in the art. The current is dependent on the electrode resistance, the electrode tissue interface (likely appreciable) and the impedance of the tissue itself, is illustratively at around 1 kohm.

In further embodiments of the invention we incorporate a wearable tsDCS controller that modulates descending autonomic signals traversing the spinal cord. In some embodiments, this is combined with an implanted electrode that directly stimulates the nerve to a targeted effector organ. This stimulation is selected as either excitatory or inhibitory, and is further embodiments depends on stimulation frequency as well as pulse amplitude and duration. The implanted electrode is in wireless communication with the wearable tsDCS controller.

This approach is sufficient for certain applications. In other applications, it is beneficial to directly modulate central autonomic outflow before spinal level modulation via tsDCS. In practice of the invention, we increase or decrease sympathetic outflow, or increase or decrease parasympathetic outflow, as a person skilled in the art would appreciate. Furthermore in particular embodiments we provide non-invasive and non-pharmacological modulating of autonomic outflow for control and treatment of autonomically-related functions and disorders.

Computer

This disclosure includes description by way of example of a device configured to execute functions (hereinafter referred to as computing device) which may be used with the presently disclosed subject matter. The description of the various components of a computing device is not intended to represent any particular architecture or manner of interconnecting the components. Other systems that have fewer or more components may also be used with the disclosed subject matter. A communication device may constitute a form of a computing device and may at least include a computing device. The computing device may include an inter-connect (e.g., bus and system core logic), which can interconnect such components of a computing device to a data processing device, such as a processor(s) or microprocessor(s), or other form of partly or completely programmable or pre-programmed device, e.g., hard wired and or application specific integrated circuit ("ASIC") customized logic circuitry, such as a controller or microcontroller, a digital signal processor, or any other form of device that can fetch instructions, operate on pre-loaded/pre-programmed instructions, and/or followed instructions found in hard-wired or customized circuitry to carry out logic operations that, together, perform steps of and whole processes and functionalities as described in the present disclosure.

In this description, various functions, functionalities and/or operations may be described as being performed by or caused by software program code to simplify description. However, those skilled in the art will recognize what is meant by such expressions is that the functions result from execution of the program code/instructions by a computing device as described above, e.g., including a processor, such as a microprocessor, microcontroller, logic circuit or the like. Alternatively, or in combination, the functions and operations can be implemented using special purpose circuitry, with or without software instructions, such as using Application-Specific Integrated Circuit (ASIC) or Field-Programmable Gate Array (FPGA), which may be programmable, partly programmable or hard wired. The application specific integrated circuit ("ASIC") logic may be such as gate arrays or standard cells, or the like, implementing customized logic by metalization(s) interconnects of the base gate array ASIC architecture or selecting and providing metalization(s) interconnects between standard cell functional blocks included in a manufacturer's library of functional blocks, etc. Embodiments can thus be implemented using hardwired circuitry without program software code/instructions, or in combination with circuitry using programmed software code/instructions.

Thus, the techniques are limited neither to any specific combination of hardware circuitry and software, nor to any particular tangible source for the instructions executed by the data processor(s) within the computing device. While some embodiments can be implemented in fully functioning computers and computer systems, various embodiments are capable of being distributed as a computing device including, e.g., a variety of forms and capable of being applied regardless of the particular type of machine or tangible computer-readable media used to actually effect the performance of the functions and operations and/or the distribution of the performance of the functions, functionalities and/or operations.

The interconnect may connect the data processing device to define logic circuitry including memory. The interconnect may be internal to the data processing device, such as coupling a microprocessor to on-board cache memory or external (to the microprocessor) memory such as main memory, or a disk drive or external to the computing device, such as a remote memory, a disc farm or other mass storage device, etc. Commercially available microprocessors, one or more of which could be a computing device or part of a computing device, include a PA-RISC series microprocessor from Hewlett-Packard Company, an 80x86 or Pentium series microprocessor from Intel Corporation, a PowerPC microprocessor from IBM, a Sparc microprocessor from Sun Microsystems, Inc, or a 68xxx series microprocessor from Motorola Corporation as examples.

The inter-connect in addition to interconnecting such as microprocessor(s) and memory may also interconnect such elements to a display controller and display device, and/or to other peripheral devices such as input/output (I/O) devices, e.g., through an input/output controller(s). Typical I/O devices can include a mouse, a keyboard(s), a modem(s), a network interface(s), printers, scanners, video cameras and other devices which are well known in the art. The interconnect may include one or more buses connected to one another through various bridges, controllers and/or adapters. In one embodiment the I/O controller includes a USB (Universal Serial Bus) adapter for controlling USB peripherals, and/or an IEEE-1394 bus adapter for controlling IEEE-1394 peripherals.

The memory may include any tangible computer-readable media, which may include but are not limited to recordable and non-recordable type media such as volatile and non-volatile memory devices, such as volatile RAM (Random Access Memory), typically implemented as dynamic RAM (DRAM) which requires power continually in order to refresh or maintain the data in the memory, and non-volatile RAM (Read Only Memory), and other types of non-volatile memory, such as a hard drive, flash memory, detachable memory stick, etc. Non-volatile memory typically may include a magnetic hard drive, a magnetic optical drive, or an optical drive (e.g., a DVD RAM, a CD RAM, a DVD or a CD), or 'other type of memory system which maintains data even after power is removed from the system.

For the purposes of describing and defining the present teachings, it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

While these teachings have been described in terms of specific embodiments, it is evident in view of the foregoing description that numerous alternatives, modifications and variations will be apparent to those skilled in the art. Accordingly, these teachings are intended to encompass all such alternatives, modifications and variations which fall within the scope and spirit of the present teachings and the following claims. The foregoing description is illustrative validation of the present invention. It will now be appreciated that tsDCS stimulation according to embodiments of the invention can be practiced non-invasively or invasively using direct current stimulation to modulate spinal cord neurons. While these teachings have been described in terms of specific embodiments, it is evident in view of the foregoing description that numerous alternatives, modifications and variations will be apparent to those skilled in the art. Accordingly, these teachings are intended to encompass all such alternatives, modifications and variations which fall within the scope and spirit of the present teachings and the following claims.

What is claimed is:

1. A method for modulating activity of an autonomically-innervated effector organ in a vertebrate being, the method comprising the steps of:
   identifying a spinal circuit between a spinal location and a return location of a vertebrate being, said spinal location associated with spinal efferent neural outflow to an autonomically-innervated effector organ of interest of said being; and
   delivering non-varying, constant direct current to said spinal circuit between said spinal location and said return location for effecting trans-spinal direct current stimulation of said efferent neural outflow to modulate activity of said organ; and applying a second direct current to a nerve providing neural control of at least one muscle associated with said organ;
wherein the activity of said organ is bladder function;
wherein modulating said bladder function is for treating a condition selected from the group consisting of urinary retention and urinary incontinence; and
wherein said treating urinary incontinence comprises anodal trans-spinal direct current stimulation at a spinal level of S2-S4 to decrease parasympathetic tone and said nerve is selected from the group consisting of pelvic splanchnic nerve and pudendal nerve.

2. The method of claim 1, further comprising:
modulating central autonomic outflow of said being to said spinal location to affect said spinal outflow.

3. The method of claim 1, further comprising:
modulating central autonomic outflow to said spinal location to affect said spinal outflow.

4. The method of claim 1, wherein the activity of said organ is bladder function.

5. The method of claim 4, wherein said modulating of spinal outflow is associated with modulation of said bladder function for treating a condition selected from the group consisting of urinary retention and urinary incontinence.

6. The method of claim 5, wherein the efferent neural outflow to the bladder is selected from the group consisting of sympathetic and parasympathetic activity.

7. The method of claim 5, wherein said treating urinary incontinence comprises anodal trans-spinal direct current stimulation at a spinal level of S2-S4 to decrease parasympathetic tone.

8. The method of claim 5, wherein said treating urinary retention comprises cathodal trans-spinal direct current stimulation at a spinal level of S2-S4 to increase parasympathetic tone.

9. The method of claim 5 wherein said treating urinary incontinence comprises cathodal trans-spinal direct current stimulation at a spinal level of T11-L2 to increase sympathetic tone.

10. The method of claim 5, wherein said treating urinary retention comprises anodal trans-spinal direct current stimulation at a spinal level of T11-L2 to decrease sympathetic tone.

11. The method of claim 1, wherein said trans-spinal direct current stimulation is applied using skin surface electrodes.

12. The method of claim 1, wherein said trans-spinal direct current stimulation is applied using at least one implanted electrode.

13. The method of claim 1, wherein said treating urinary retention comprises cathodal trans-spinal direct current stimulation at a spinal level of S2-S4 to increase parasympathetic tone and said nerve is selected from the group consisting of pelvic splanchnic nerve and pudendal nerve.

14. The method of claim 1, wherein said treating urinary incontinence comprises cathodal trans-spinal direct current stimulation at a spinal level of T11-L2 to increase sympathetic tone and said nerve is selected from the group consisting of pelvic splanchnic nerve and pudendal nerve.

15. The method of claim 1, wherein said treating urinary retention comprises anodal trans-spinal direct current stimulation at a spinal level of T11-L2 to decrease sympathetic tone and said nerve is selected from the group consisting of pelvic splanchnic nerve and pudendal nerve.

16. The method of claim 1, wherein said trans-spinal direct current is applied using skin surface electrodes and said second direct current is applied using implanted electrodes.

17. The method of claim 2, wherein the activity of said organ is bladder function; and wherein modulating bladder function is applied for treating a condition selected from the set of urinary retention and urinary incontinence.

18. The method of claim 17, wherein said treating urinary retention comprises cathodal trans-spinal direct current stimulation at a spinal level of S2-S4 to increase parasympathetic tone, said nerve is selected from the group consisting of pelvic splanchnic nerve and pudendal nerve, wherein said second direct current is pulsed, and said modulating central autonomic outflow includes application of at least one of the group consisting of transcranial direct current stimulation, transcranial magnetic stimulation, transcutaneous vagal nerve stimulation, application of heat to a thermosensitive area of skin, and administering a parasympathomimetic pharmacological agent.

19. The method of claim 17, wherein said treating urinary incontinence comprises cathodal trans-spinal direct current stimulation at a spinal level of T11-L2 to increase sympathetic tone, said nerve is selected from the group consisting of pelvic splanchnic nerve and pudendal nerve, wherein said second direct current is pulsed, and said modulating central autonomic outflow includes application of at least one of the group consisting of transcranial direct current stimulation, transcranial magnetic stimulation, application of cold to a thermosensitive area of skin, and administering a sympathomimetic pharmacological agent.

20. The method of claim 17, wherein said treating urinary retention comprises anodal trans-spinal direct current stimulation at a spinal level of T11-L2 to decrease sympathetic tone, said nerve is selected from the group consisting of pelvic splanchnic nerve and pudendal nerve, wherein said second direct current is pulsed, and said modulating central autonomic outflow includes application of at least one of the group consisting of transcranial direct current stimulation, transcranial magnetic stimulation, application of heat to a thermosensitive area of skin, transcutaneous vagal nerve stimulation, and administering a sympatholytic pharmacological agent.

21. The method of claim 3, wherein the activity of said organ is bladder function; and wherein modulating bladder function is for treating a condition selected from the group consisting of urinary retention and urinary incontinence.

22. The method of claim 21, wherein said treating urinary incontinence comprises anodal trans-spinal direct current stimulation at a spinal level of S2-S4 to decrease parasympathetic tone and said modulating central autonomic outflow includes application of at least one of the group consisting of transcranial direct current stimulation, transcranial magnetic stimulation, application of cold to a thermosensitive area of skin, and administering a parasympatholytic pharmacological agent.

23. The method of claim 21, wherein said treating urinary retention comprises cathodal trans-spinal direct current stimulation at a spinal level of S2-S4 to increase parasympathetic tone and said modulating central autonomic outflow includes application of at least one of the group consisting of transcranial direct current stimulation, transcranial magnetic stimulation, transcutaneous vagal nerve stimulation, application of heat to a thermosensitive area of skin, and administering a parasympathomimetic pharmacological agent.

24. The method of claim 21, wherein said treating urinary incontinence comprises cathodal trans-spinal direct current stimulation at a spinal level of T11-L2 to increase sympathetic tone and said modulating central autonomic outflow includes application of at least one of the group consisting of transcranial direct current stimulation, transcranial magnetic stimulation, application of cold to a thermosensitive area of skin, and administering a sympathomimetic pharmacological agent.

25. The method of claim 21, wherein said treating urinary retention comprises anodal trans-spinal direct current stimulation at a spinal level of T11-L2 to decrease sympathetic tone and said modulating central autonomic outflow includes application of at least one of the group consisting of transcranial direct current stimulation, transcranial magnetic stimulation, application of heat to a thermosensitive area of skin, transcutaneous vagal nerve stimulation, and administering a sympatholytic pharmacological agent.

26. A method for modulating activity of an autonomically-innervated effector organ in a vertebrate being, the method comprising the steps of:
    identifying a spinal circuit between a spinal location and a return location of a vertebrate being, said spinal location associated with spinal efferent neural outflow to an autonomically-innervated effector organ of interest of said being;
    delivering non-varying, constant direct current to said spinal circuit between said spinal location and said return location for effecting trans-spinal direct current stimulation of said efferent neural outflow to modulate activity of said organ; and
    modulating central autonomic outflow of said being to said spinal location to affect said spinal outflow;
    wherein the activity of said organ is bladder function; and
    wherein modulating bladder function is applied for treating a condition selected from the set of urinary retention and urinary incontinence; and
    wherein said treating urinary incontinence comprises anodal trans-spinal direct current stimulation at a spinal level of S2-S4 to decrease parasympathetic tone, said nerve is selected from the group consisting of pelvic splanchnic nerve and pudendal nerve, wherein said second direct current is pulsed, and said modulating central autonomic outflow includes application of at least one of the group consisting of transcranial direct current stimulation, transcranial magnetic stimulation, application of cold to a thermosensitive area of skin, and administering a parasympatholytic pharmacological agent.

* * * * *

UNITED STATES PATENT AND TRADEMARK OFFICE
CERTIFICATE OF CORRECTION

| | |
|---|---|
| PATENT NO. | : 9,707,391 B2 |
| APPLICATION NO. | : 15/190088 |
| DATED | : July 18, 2017 |
| INVENTOR(S) | : Zaghloul Ahmed |

It is certified that error appears in the above-identified patent and that said Letters Patent is hereby corrected as shown below:

On the Title Page

Under (56) References Cited, the following should be listed under "U.S. PATENT DOCUMENTS":
2006/0052826 A1 3/2006 Kim et al.
2006/0122660 A1 6/2006 Boveja et al.
2008/0071321 A1 3/2008 Boggs II et al.
2013/0053922 A1 2/2013 Ahmed et al.
2015/0073232 A1 3/2015 Ahmad et al.

Signed and Sealed this
Twenty-seventh Day of March, 2018

Andrei Iancu
*Director of the United States Patent and Trademark Office*